US009193972B2

(12) United States Patent
Shanklin et al.

(10) Patent No.: US 9,193,972 B2
(45) Date of Patent: Nov. 24, 2015

(54) COMBINED HAIRPIN-ANTISENSE COMPOSITIONS AND METHODS FOR MODULATING EXPRESSION

(71) Applicant: BROOKHAVEN SCIENCE ASSOCIATES, LLC, Upton, NY (US)

(72) Inventors: John Shanklin, Shoreham, NY (US); Tam Huu Nguyen, Lincoln, NE (US)

(73) Assignee: Brookhaven Science Associates, LLC, Upton, NY (US)

( * ) Notice: Subject to any disclaimer, the term of this patent is extended or adjusted under 35 U.S.C. 154(b) by 0 days.

(21) Appl. No.: 14/452,049

(22) Filed: Aug. 5, 2014

(65) Prior Publication Data

US 2014/0342453 A1 Nov. 20, 2014

Related U.S. Application Data

(63) Continuation of application No. 12/052,658, filed on Mar. 20, 2008, now Pat. No. 8,796,442.

(60) Provisional application No. 60/896,212, filed on Mar. 21, 2007.

(51) Int. Cl.

| C07H 21/04 | (2006.01) |
|---|---|
| C12N 15/113 | (2010.01) |
| C12N 15/11 | (2006.01) |
| C12N 15/82 | (2006.01) |

(52) U.S. Cl.
CPC ............ *C12N 15/113* (2013.01); *C12N 15/111* (2013.01); *C12N 15/8218* (2013.01); *C12N 15/8247* (2013.01); *C12N 2310/11* (2013.01); *C12N 2310/14* (2013.01); *C12N 2310/3519* (2013.01); *C12N 2310/53* (2013.01)

(58) Field of Classification Search
None
See application file for complete search history.

(56) References Cited

U.S. PATENT DOCUMENTS

| 5,759,829 A | 6/1998 | Shewmaker et al. |
|---|---|---|
| 5,952,657 A | 9/1999 | Alexander et al. |
| 6,380,477 B1 | 4/2002 | Curtin |
| 6,395,713 B1 | 5/2002 | Beigelman et al. |
| 6,506,559 B1 | 1/2003 | Fire et al. |
| 6,653,458 B1 | 11/2003 | Manoharan et al. |
| 2002/0058815 A1 | 5/2002 | Liu et al. |
| 2002/0137210 A1 | 9/2002 | Churikov |
| 2003/0130186 A1 | 7/2003 | Vargeese et al. |
| 2003/0175965 A1 | 9/2003 | Lowe et al. |
| 2003/0180945 A1 | 9/2003 | Wang et al. |
| 2003/0180955 A1 | 9/2003 | Ozasa et al. |
| 2004/0053875 A1 | 3/2004 | Kreutzer et al. |
| 2004/0053876 A1 | 3/2004 | Turner et al. |
| 2006/0063174 A1 | 3/2006 | Turner et al. |
| 2008/0311658 A1 | 12/2008 | Shanklin et al. |

FOREIGN PATENT DOCUMENTS

| EP | 1144623 B1 | 8/2002 |
|---|---|---|
| JP | 06502758 A | 3/1994 |
| JP | 2005519607 A | 7/2005 |
| WO | 9907409 A1 | 2/1999 |
| WO | 9932619 A1 | 7/1999 |
| WO | 9949029 A1 | 9/1999 |
| WO | 9953050 A1 | 10/1999 |
| WO | 9959029 A1 | 11/1999 |
| WO | 9961631 A1 | 12/1999 |
| WO | 0001846 A2 | 1/2000 |
| WO | 0044914 A1 | 8/2000 |
| WO | 0059035 A1 | 10/2000 |
| WO | 0063364 A2 | 10/2000 |
| WO | 0104313 A1 | 1/2001 |
| WO | 0129058 A1 | 4/2001 |
| WO | 0136646 A1 | 5/2001 |
| WO | 0138551 A1 | 5/2001 |
| WO | 0142443 A1 | 6/2001 |
| WO | 0153475 A2 | 7/2001 |
| WO | 0168836 A2 | 9/2001 |
| WO | 0170944 A2 | 9/2001 |
| WO | 0170949 A1 | 9/2001 |
| WO | 0172774 A2 | 10/2001 |
| WO | 0192513 A1 | 12/2001 |
| WO | 0238805 A2 | 5/2002 |
| WO | 0244321 A2 | 6/2002 |
| WO | 02055692 A2 | 7/2002 |
| WO | 02055693 A2 | 7/2002 |

OTHER PUBLICATIONS

Allshire, Robin, RNAi and Heterochromatin: A Hushed-up Affair, Science, New Series, Sep. 13, 2002, pp. 1818-1819, vol. 297, American Association for the Advancement of Science.
Bahramian, Mohammad, et al., Transcriptional and Post-transcriptional Silencing of Rodent a1(I) Collagen by a Homologous Transcriptionally Self-Silenced Transgene, Molecular and Cellular Biology, Jan. 1999, pp. 274-283, vol. 19, No. 1, American Society for Microbiology.
Bass, Brenda L., RNA Interference The Short Answer, Nature, May 24, 2001, pp. 428-, vol. 411, Macmillan Magazines Ltd.
Bernsten, Emily, et al., Role for a Bidentate Ribonuclease in the Initiation Step of RNA Interference, Nature, Jan. 18, 2001, p. 363-366, vol. 409, Macmillan Magazines Ltd.

(Continued)

*Primary Examiner* — Kimberly Chong
(74) *Attorney, Agent, or Firm* — TraskBritt, P.C.

(57) ABSTRACT

A nucleotide construct comprising a nucleotide sequence that forms a stem and a loop, wherein the loop comprises a nucleotide sequence that modulates expression of a target, wherein the stem comprises a nucleotide sequence that modulates expression of a target, and wherein the target modulated by the nucleotide sequence in the loop and the target modulated by the nucleotide sequence in the stem may be the same or different. Vectors, methods of regulating target expression, methods of providing a cell, and methods of treating conditions comprising the nucleotide sequence are also disclosed.

41 Claims, 15 Drawing Sheets

(56) References Cited

OTHER PUBLICATIONS

Chen et al., "Transdermal protein delivery by a coadministered peptide identified via phage display," Nature Biotechnology, vol. 24, No. 4, pp. 455-460, 2006.
Chuang, Chiou-Fen, et al., Specific and Heritable Genetic Interference by Double-Stranded RNA in Arabidopsis Thaliana, PNAS, Apr. 25, 2000, pp. 5985-5990. vol. 97, No. 9.
Elbashir, Sayda M., et al., Duplexes of 21-Nucleotide RNAs Mediate RNA Interference in Cultured Mammalian Cells, Nature, May 24, 2001, pp. 494-498, vol. 411, Macmillan Magazines Ltd.
Eddy and Durbin, "RNA Sequence analysis using covariance models," Nucleic Acids Research, 1994, vol. 22, No. 11 pp. 2079-2088 (http://www.gentiecs.Wustl.edu/eddy/software/).
Elbashir, Sayda M., et al., RNA Interference is Mediated by 21- and 22-Nucleotide RNAs, Genes & Dev., 2001, pp. 188-200, vol. 15, Cold Spring Harbor Laboratory Press.
Fire, Andrew, RNA-Triggered Gene Silencing, TIG, Sep. 1999, pp. 358-363, vol. 15, No. 9.
Fire, Andrew, et al., Potent and Specific Genetic Interference by Double-Stranded RNA in Caenorhabditis Elegans, Nature, Feb. 19, 1998, pp. 806-811, Macmillan Publishers Ltd.
Freier, Susan M., et al., Improved Free-Energy Parameters for Predictions of RNA Duplex Stability, Proc. Natl. Acad. Sci. USA, Dec. 1986, pp. 9373-9377, vol. 83.
Gorodkin, J., et al., Finding the Most Significant Common Sequence and Structure Motifs in a Set of RNA Sequences, Nucleic Acids Research, 1997, pp. 3724-3732, vol. 25, No. 18, Oxford University Press.
Gorodkin, "Finding Common Sequence and Structure Motifs in a set of RNA Sequences," ISMB, 1997, vol. 5, pp. 120-123.
Hamilton, Andrew J., et al., A Species of Small Antisense RNA in Posttranscriptional Gene Silencing in Plants, Science, Oct. 29, 1999, pp. 950-952, vol. 286.
Hammond, Scott M., et al., An RNA-Directed Nuclease Mediates Post-Transcriptional Gene Silencing in Drosophila Cells, Nature, Mar. 16, 2000, pp. 293-296, vol. 404, Macmillan Magazines Ltd.
Hall, Ira M., et al., Establishment and Maintenance of a Heterochromatin Domain, Science, New Series, Sep. 27, 2002, pp. 2232-2237, vol. 297, No. 5590, American Association for the Advancement of Science.
Hutvagner, Gyorgy, et al., A MicroRNA in a Multiple-Turnover RNAi Enzyme Complex, Science, New Series, Sep. 20, 2002, pp. 2056-2060, vol. 297, No. 5589, American Association for the Advancement of Science.
Hutvagner, Gyorgy, et al., A Cellular Function for the RNA-Interference Enzyme Dicer in the Maturation of the let-7 Small Temporal RNA, Science, New Series, Aug. 3, 2001, pp. 834-838, vol. 293, No. 5531, American Association for the Advancement of Science.
Jenuwein, Thomas, An RNA-Guided Pathway for the Epigenome, Science, New Series, Sep. 27, 2002, pp. 2215-2218, vol. 297, No. 5590, American Association for the Advancement of Science.
Liu, Qing, et al., High-Stearic and High Oleic Cottonseed Oils Produced by Hairpin RNA-Mediated Post Transcriptional Gene Silencing, Plant Physiology, Aug. 2002, pp. 1732-1753, vol. 129, American Society of Plant Biologists.
Loakes, David, The Applications of Universal DNA Base Analogues, Nucleic Acids Research, 2001, pp. 2437-2447, vol. 29, No. 12, Oxford University Press.
Martinez et al, "Single-Stranded Antisense siRNAs Guide Target RNA Cleavage in RNAi," Cell, Sep. 6, 2002, vol. 110. Pages 563-574.
McManus, M.T., et al., Gene Silencing Using Micro-RNA Designed Hairpins, RNA, 2002, pp. 842-850, vol. 8, RNA Society.
Menendez et al., Inhibition of fatty acid synthase (FAS) suppresses HER2/neu 9ergG-2) oncogene overexpression in cancer cells. PNAS, Jul. 2004, 10715-10720.
Miyagishi, Makoto, et al., Strategies for Generation of an siRNA Expression Library Directed Against the Human Genome, Oligonucleotides, 2003, pp. 325-333, vol. 13.
Pandolfini, Tiziana, et al., Expression of Self-Complementary Hairpin RNA Under the Control of the roIC Promoter Confers Systemic Disease Resistance to Plum Pox Virus Without Preventing Local Infection, BMC Biotechnology, Jun. 25 2003, pp. 1-15, vol. 7, No. 3.
Reinhart, Brenda J., et al., Small RNAs Correspond to Centromere Heterochromatic Repeats, Science, New Series, Sep. 13, 2002, p. 1831, vol. 297, No. 5588, American Association for the Advancement of Science.
Reinhart, Brenda J., et al., MicroRNAs in Plants, Genes & Development, 2002, pp. 1616-1626, vol. 16, Cold Spring Harbor Laboratory Press.
Stoutjesdijk, Peter A., et al., hpRNA-Mediated Targeting of the Arabidopsis FAD2 Gene Gives Highly Efficient and Stable Silencing, Plant Physiology, Aug. 2002, pp. 1723-1731, vol. 129, American Society of Plant Biologists.
Smith, Neil A., et al., Total Silencing by Intron-Spliced Haripin RNAs, Nature, Sep. 21, 2000, pp. 319-320, vol. 407, Macmillan Magazines Ltd.
Schwarz et al., "Evidence that siRNAs Function as Guides, Not Primers, in the Drosohila and Human RNAi Pathways," Molecular Cell, Sep. 2002, vol. 10, pp. 537-568.
Volpe, Thomas A., et al., Regulation of Heterochromatic Silencing and Histone H3 Lysine-9 Methylation by RNAi, Science, New Series, Sep. 13, 2002, pp. 1833-1837, vol. 297, American Association for the Advancement of Science.
Waterhouse, Peter M., et al., Exploring Plant Genomes by RNA-Induced Gene Silencing, Nature Reviews. Genetics, Jan. 2003, pp. 29-38, vol. 4, Nature Publishing Group.
Waterhouse, Peter M., et al., Virus Resistance and Gene Silencing in Plants Can Be Induced by Simultaneous Expression of Sense and Antisense RNA, Proc. Natl. Acad. Sci., Nov. 1998, pp. 13959-13964, vol. 95, The National Academy of Sciences.
Wesley, S. Varsha, et al., Construct Design for Efficient, Effective and High-Throughput Gene Silencing in Plants, The Plant Journal, 2001, pp. 581-590, vol. 27, No. 6, Blackwell Science Ltd.
Wianny, Florence, et al., Specific Interference with Gene Function by Double-Stranded RNA in Early Mouse Development, Nature Cell Biology, Feb. 2000, pp. 70-75, vol. 2, Macmillan Magazines Ltd.
Database Medline [Online] US National Library of Medicine (NLM), Bethesda, MD, US; Jan. 2007, Yan Fei et al: "[Transgenic wheat expressing virus-derived hairpin RNA is resistant to Barley yellow dwarf virus]" XP002595601 Database accession No. NLM17284432 & Yi Chuan = Hereditas / Zhongguo Yi Chuan Xue Hui Bian Ji Jan. 2007 LNKD—PUBMED:17284432, vol. 29, No. 1, Jan. 2007, pp. 97-102, ISSN: 0253-9772, abstract only.
Pidkowich Mark S et al: "Modulating seed beta-ketoacyl-acyl carrier protein synthase II level converts the composition of a temperate seed oil to that of a palm-like tropical oil" Proceedings of the National Academy of Sciences of the United States of America, vol. 104, No. 11, Mar. 13, 2007, pp. 4742-4747, XP002595602 ISSN: 0027-8424.
Parrish et al., "Functional anatomy of a dsRNA trigger: differnential requirement for the two trigger strands in RNA interference," Molecular Cell, Nov. 2000, pp. 1077-1078, vol. 6.
Usman et al., U.S. Appl. No. 60/402,996, filed Aug. 13, 2002.
Zhang, et al., "Transgenic wheat expressing virus-derived hairpin RNA is resistant to Barley yellow dwarf virus," Hereditas, 2007, pp. 97-102, vol. 29, No.
PCT International Search Report for International Application No. PCT/US2008/57704, mailed Sep. 12, 2008.
PCT Written Opinion for International Application No. PCT/US2008/57704, mailed Sep. 12, 2008.
PCT International Preliminary Report on Patentability for International Application No. PCT/US2008/57704, mailed Sep. 22, 2009.

COMBINED HAIRPIN-ANTISENSE COMPOSITIONS AND METHODS FOR MODULATING EXPRESSION

CROSS-REFERENCE TO RELATED APPLICATION

This application is a continuation of U.S. patent application Ser. No. 12/052,658, filed Mar. 20, 2008, which will issue as U.S. Pat. No. 8,796,442 on Aug. 5, 2014, which is a utility conversion of U.S. Provisional Patent Application Ser. No. 60/896,212, filed Mar. 21, 2007.

STATEMENT REGARDING FEDERALLY SPONSORED RESEARCH OR DEVELOPMENT

The present invention was made with government support under Grant No. DE-AC02-98CH10886 awarded by the U.S. Department of Energy. The United States government has certain rights in the invention.

TECHNICAL FIELD

This invention relates generally to the field of biology. More specifically, aspects of this invention relate to the control of gene expression.

BACKGROUND

Antisense suppression refers to the binding of an "antisense" strand of a nucleic acid to a gene or mRNA, thereby preventing expression of the gene or translation of the mRNA. Typically for antisense suppression, an expression cassette is designed to express an RNA molecule complementary to all or part of an mRNA encoding a target. Over-expression of the antisense RNA molecule may result in reduced expression of the native gene.

The polynucleotide for use in antisense suppression may correspond to all or part of the complement of the sequence encoding the target, all or part of the complement of the 5' and/or 3' untranslated region of the target transcript, and/or all or part of the complement of both the coding sequence and the untranslated regions of a transcript encoding the target. In addition, the antisense polynucleotide may be fully complementary (i.e., 100% identical to the complement of the target sequence) or partially complementary (i.e., less than 100% identical to the complement of the target sequence) to the target sequence. Antisense suppression may be used to inhibit the expression of multiple proteins in the same cell or organism, as described, for example, in U.S. Pat. No. 5,952,657. Furthermore, portions of the antisense nucleotides may be used to disrupt the expression of the target gene. Generally, sequences of at least 50, 100, 200, 300, 500, or 550 nucleotides may be used. Methods for using antisense suppression to inhibit the expression of endogenous genes in plants are described, for example, in Liu et al. (2002), Plant Physiol. 129:1732-1753 and U.S. Pat. Nos. 5,759,829 and 5,952,657, each of which is herein incorporated by reference. Efficiency of antisense suppression may be increased by including a poly-dT region in the expression cassette at a position 3' to the antisense sequence and 5' of the polyadenylation signal. See, U.S. Patent Publication No. 20020058815, herein incorporated by reference.

RNA interference refers to the process of sequence-specific post-transcriptional gene silencing in animals mediated by short interfering RNAs (siRNAs) (Fire et al., 1998, Nature 391, 806; Hamilton et al., 1999, Science 286, 950-951). The corresponding process in plants is commonly referred to as post-transcriptional gene silencing or RNA silencing, and is also referred to as quelling in fungi. The process of post-transcriptional gene silencing is thought to be an evolutionarily conserved cellular defense mechanism used to prevent the expression of foreign genes and is commonly shared by diverse flora and phyla (Fire et al., 1999, Trends Genet. 15, 358). Such protection from foreign gene expression may have evolved in response to the expression of double-stranded RNAs (dsRNAs) derived from viral infection or from the random integration of transposon elements into a host genome via a cellular response that specifically destroys homologous single-stranded RNA or viral genomic RNA. The presence of dsRNA in cells triggers the RNAi response through a mechanism that has yet to be fully characterized. This mechanism appears to be different from the interferon response that results from dsRNA-mediated activation of protein kinase PKR and 2', 5'-oligoadenylate synthetase resulting in non-specific cleavage of mRNA by ribonuclease L.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Hamilton et al., supra; Berstein et al., 2001, Nature 409, 363). Short interfering RNAs derived from dicer activity are typically about 21 to about 23 nucleotides in length and comprise about 19 base pair duplexes (Hamilton et al., supra; Elbashir et al., 2001, Genes Dev. 15, 188). Dicer has also been implicated in the excision of 21- and 22-nucleotide small temporal RNAs (stRNAs) from precursor RNA of conserved structure that are implicated in translational control (Hutvagner et al., 2001, Science 293, 834). The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex (Elbashir et al., 2001, Genes Dev. 15, 188).

RNAi has been studied in a variety of systems. Fire et al., 1998, Nature 391, 806, were the first to observe RNAi in C. elegans. Bahramian and Zarbl, 1999, Molecular and Cellular Biology 19, 274-283, and Wianny and Goetz, 1999, Nature Cell Biol. 2, 70, describe RNAi mediated by dsRNA in mammalian systems. Hammond et al., 2000, Nature 404, 293, describe RNAi in Drosophila cells transfected with dsRNA. Elbashir et al., 2001, Nature 411, 494, describe RNAi induced by introduction of duplexes of synthetic 21-nucleotide RNAs in cultured mammalian cells including human embryonic kidney and HeLa cells. Methods for using dsRNA interference to inhibit the expression of endogenous plant genes are described in Waterhouse et al. (1998), Proc. Natl. Acad. Sci. USA 95:13959-13965, Liu et al. (2002), Plant Physiol. 129: 1732-1753, and WO 99/59029, WO 99/53050, WO 99/61631, and WO 00/59035.

Additional RNAi methods relating to the inhibition of the expression of one or more targets obtained by hairpin RNA (hpRNA) interference or intron-containing hairpin RNA (ihpRNA) interference have been described. These methods are highly efficient at inhibiting the expression of endogenous genes. See, Waterhouse and Helliwell (2003) Nat. Rev. Genet. 5:29-38 and the references cited therein.

For hpRNA interference, the expression cassette is designed to express an RNA molecule that hybridizes with itself to form a hairpin structure that comprises a single-stranded loop region and a base-paired stem. The base-paired stem region comprises a sense sequence corresponding to all or part of the endogenous messenger RNA encoding the gene whose expression is to be inhibited, and an antisense sequence that is fully or partially complementary to the sense sequence. Thus, the base-paired stem region of the molecule generally determines the specificity of the RNA interference. hpRNA molecules are highly efficient at inhibiting the expression of endogenous genes, and the RNA interference they induce is inherited by subsequent generations. See, for example, Chuang and Meyerowitz (2000) *Proc. Natl. Acad. Sci. USA* 97:5985-5990; Stoutjesdijk et al. (2002), *Plant Physiol.* 129:1723-1731; and Waterhouse and Helliwell (2003) *Nat. Rev. Genet.* 5:29-38. Methods for using hpRNA interference to inhibit or silence the expression of genes are described, for example, in Chuang and Meyerowitz (2000) *Proc. Natl. Acad. Sci. USA* 97:5985-5990; Stoutjesdijk et al. (2002), *Plant Physiol.* 129:1723-1731; Waterhouse and Helliwell (2003) *Nat. Rev. Genet.* 5:29-38; Pandolfini et al., *BMC Biotechnology* 3:7, and U.S. Patent Publication No. 20030175965. A transient assay for the efficiency of hpRNA constructs to silence gene expression in vivo has been described by Panstruga et al. (2003), *Mol. Biol. Rep.* 30:135-150.

For ihpRNA, the interfering molecules have the same general structure as for hpRNA, but the RNA molecule additionally comprises an intron that is capable of being spliced in the cell in which the ihpRNA is expressed. The use of an intron minimizes the size of the loop in the hairpin RNA molecule following splicing, which increases the efficiency of interference. See, for example, Smith et al. (2000), *Nature* 507:319-320. In fact, Smith et al. show 100% suppression of endogenous gene expression using ihpRNA-mediated interference. Methods for using ihpRNA interference to inhibit the expression of genes are described, for example, in Smith et al. (2000), *Nature* 507:319-320; Wesley et al. (2001), *Plant J.* 27:581-590; Wang and Waterhouse (2001) *Curr. Opin. Plant Biol.* 5:156-150; Waterhouse and Helliwell (2003) *Nat. Rev. Genet.* 5:29-38; Helliwell and Waterhouse (2003) *Methods* 30:289-295, and U.S. Patent Publication No. 20030180955.

Others have reported on various RNAi and gene-silencing systems. For example, Parrish et al., 2000, *Molecular Cell* 6, 1077-1087, describe specific chemically modified siRNA constructs targeting the unc-22 gene of *C. elegans*. Grossniklaus, International PCT Publication No. WO 01/38551, describes certain methods for regulating polycomb gene expression in plants using certain dsRNAs. Churikov et al., International PCT Publication No. WO 01/42443, describe certain methods for modifying genetic characteristics of an organism using certain dsRNAs. Cogoni et al., International PCT Publication No. WO 01/53475, describe certain methods for isolating a *Neurospora*-silencing gene and uses thereof. Reed et al., International PCT Publication No. WO 01/68836, describe certain methods for gene silencing in plants. Honer et al., International PCT Publication No. WO 01/70944, describe certain methods of drug screening using transgenic nematodes as Parkinson's disease models using certain dsRNAs. Deak et al., International PCT Publication No. WO 01/72774, describe certain *Drosophila*-derived gene products that may be related to RNAi in *Drosophila*. Amdt et al., International PCT Publication No. WO 01/92513 describe certain methods for mediating gene suppression by using factors that enhance RNAi. Tuschl et al., International PCT Publication No. WO 02/44321, describe certain synthetic siRNA constructs. Pachuk et al, International PCT Publication No. WO 00/63364, and Satishchandran et al., International PCT Publication No. WO 01/04313, describe certain methods and compositions for inhibiting the function of certain polynucleotide sequences using certain dsRNAs. Echeverri et al., International PCT Publication No. WO 02/38805, describe certain *C. elegans* genes identified via RNAi. Kreutzer et al., International PCT Publications Nos. WO 02/055692, WO 02/055693, and EP 1144623 B1 describe certain methods for inhibiting gene expression using RNAi. Graham et al., International PCT Publications Nos. WO 99/49029 and WO 01/70949, and AU 4037501 describe certain vector expressed siRNA molecules. Fire et al., U.S. Pat. No. 6,506,559, describe certain methods for inhibiting gene expression in vitro using certain long dsRNA (greater than 25 nucleotides) constructs that mediate RNAi.

Although much work has been done in the area of gene silencing using RNAi and antisense technologies, improvements that allow increased modulation of gene expression over RNAi or antisense technology would be an improvement in the art.

BRIEF SUMMARY OF THE INVENTION

One example embodiment of the present invention provides a nucleotide construct, comprising: a nucleotide sequence that forms a stem and a loop; wherein the loop comprises a first nucleotide sequence that modulates expression of a target; wherein the stem comprises a second nucleotide sequence that modulates expression of a target; and wherein the target modulated by the first nucleotide sequence and the target modulated by the second nucleotide sequence may be the same or different.

In a further example embodiment, the first nucleotide sequence that modulates expression of a target modulates the expression of the target through the RNAi pathway. In an additional example embodiment, the first nucleotide sequence that modulates expression of a target modulates the expression of the target via antisense modulation of expression.

A particular embodiment of the present invention provides a nucleotide construct, comprising: a nucleotide sequence that forms a stem and a loop; and a gene of interest operably linked to a promoter, wherein the stem comprises a second nucleotide sequence that modulates expression of a target; and wherein the loop comprises a first nucleotide sequence that may or may not modulate expression of a target. In a further example embodiment, the gene of interest operably linked to a promoter is located in the loop.

Another embodiment of the present invention provides a vector comprising the sequences encoding the nucleotide sequences, as previously described. An alternative embodiment provides a vector comprising a promoter operably linked to a sequence encoding a nucleotide sequence that forms a stem and a loop; wherein the loop comprises a first nucleotide sequence that modulates expression of a target; and wherein the stem comprises a second nucleotide sequence that modulates expression of a target.

An example embodiment of the present invention provides a method of regulating the expression of a target, the method comprising: providing to a cell a sequence comprising a nucleotide sequence that forms a stem and a loop; wherein the loop comprises a first nucleotide sequence that modulates expression of the target; and wherein the stem comprises a second nucleotide sequence that modulates expression of the target; and culturing said cell.

An example embodiment of the present invention provides a method of regulating the expression of a target, the method comprising providing to a cell a vector comprising a promoter operably linked to a sequence encoding a nucleotide sequence that forms a stem and a loop; wherein the loop comprises a first nucleotide sequence that modulates expression of the target; and wherein the stem comprises a second nucleotide sequence that modulates expression of the target; and expressing the nucleotide sequence from said vector in said cell.

Another embodiment of the present invention provides a method of treating a condition in a subject comprising administering to the subject the previously described sequence comprising the nucleotide sequence that forms a stem and a loop. A particular embodiment comprises administering to the subject a vector comprising a promoter operably linked to a sequence encoding a nucleotide sequence that forms a stem and a loop.

A particular embodiment of the present invention provides a medicament comprising: a sequence comprising a nucleotide sequence that forms a stem and a loop; wherein the loop comprises a first nucleotide sequence that modulates expression of a target; and wherein the stem comprises a second nucleotide sequence that modulates expression of a target, and a pharmaceutically acceptable carrier, diluent, and/or adjuvant. An alternative embodiment of the present invention provides a medicament comprising a sequence comprising a vector that includes a promoter operably linked to a sequence encoding a nucleotide sequence that forms a stem and a loop.

An example embodiment of the present invention provides a cell comprising the previously described nucleotide sequence that forms a stem and a loop. An alternative embodiment comprises providing a cell comprising a vector that includes a promoter operably linked to a sequence encoding a nucleotide sequence that forms a stem and a loop.

An example embodiment of the present invention provides a method of making a construct for regulating a target, the method comprising: combining into a single nucleic sequence a first and second sequence capable of base pairing to form a stem-loop structure in the construct; and a third sequence, disposed between the first and second sequences; wherein said first and second sequences, when base paired, are capable of generating an siRNA; wherein said third sequence is of sufficient length to allow the first and second sequences to stably pair with each other; and wherein said third sequence comprises a sequence capable of modulating a target through antisense suppression.

An example embodiment of the present invention provides a method of making a construct for regulating a target, the method comprising: combining into a single nucleic sequence a first and second sequence capable of base pairing to form a stem-loop structure in the construct; a third sequence, disposed between the first and second sequences; and a fourth sequence comprising a gene of interest operably linked to a promoter; wherein said first and second sequences, when base paired, are capable of generating an siRNA; wherein said third sequence is of sufficient length to allow the first and second sequences to stably pair with each other; and wherein said third sequence may or may not comprise a sequence capable of modulating a target through antisense suppression.

Another embodiment of the invention provides a method of producing a plant with modified levels of endogenous component fatty acids. The method includes modulating the levels of a heterologous gene, such as a fatty acid synthesis or lipid metabolism gene.

The present invention may further be utilized in combination with various gene silencing methodologies using RNAi and antisense technologies that are known in the art to provide increased modulation of gene expression tailored to one or more specific genes and/or genetic pathways.

DETAILED DESCRIPTION OF THE INVENTION

Figure 1:
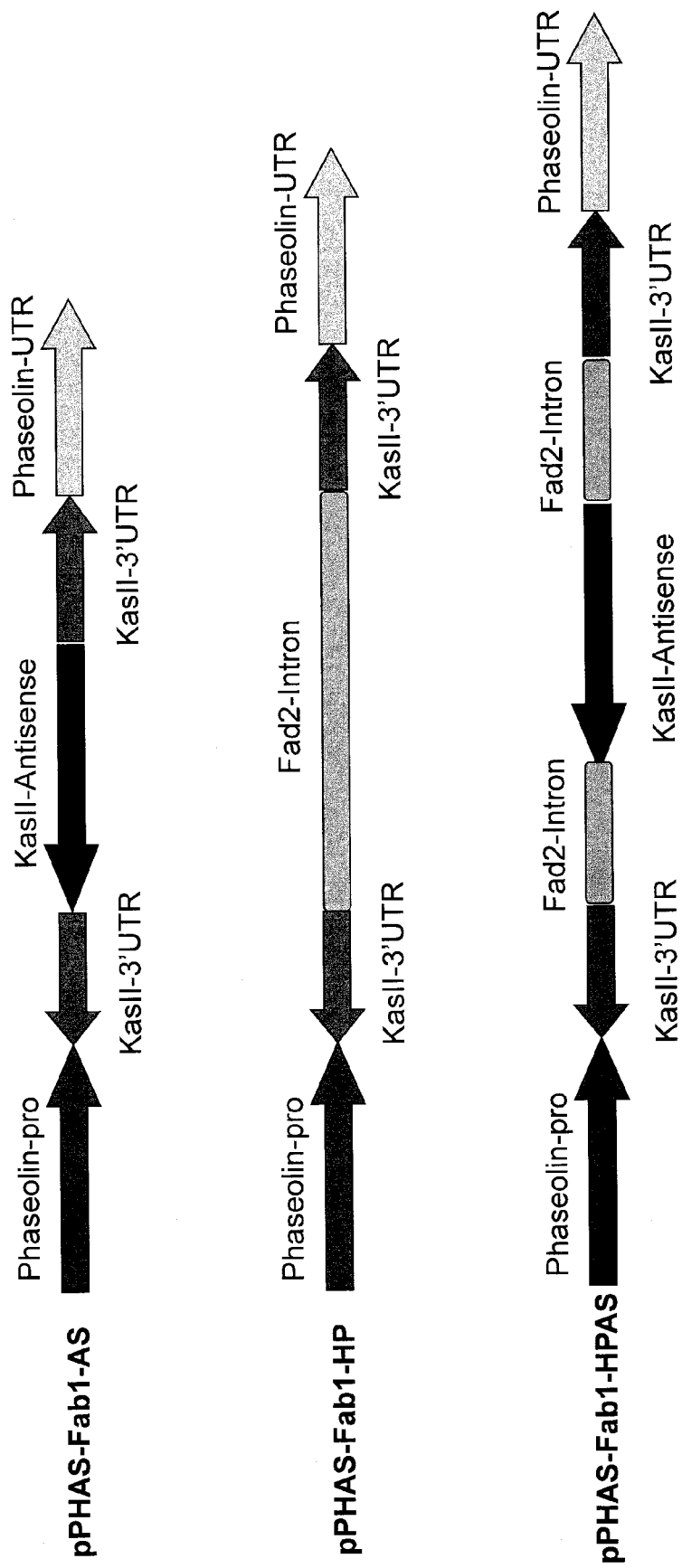
FIG. 1 is graphical representation of the constructs pPHAS-Fab1-AS, pPHAS-Fab1-HP, and pPHAS-Fab1-HPAS.

One aspect of the present invention relates to compounds, compositions, and methods useful for modulating the expression of a target in a cell. Specifically, aspects of the instant invention relate nucleotide sequences capable of modulating expression of a target, such as a gene, oligonucleotide sequence, and/or protein, by RNA inference (RNAi) and/or antisense suppression. Generally the modulating nucleotide sequence (mNS) molecules of the present invention may include a stem-loop structure, wherein the stem provides a substrate for dicer and may act to suppress a target through the RNAi pathway, and wherein the loop portion of the structure may comprise a first sequence that may act to suppress a gene through antisense suppression. The mNS molecules of the invention may be, in whole or in part, chemically modified and/or synthetically created. The use of chemically modified mNS may improve various properties of mNS molecules, for example, through increased resistance to nuclease degradation in vivo and/or improved cellular uptake. The chemically modified mNS molecules of the instant invention provide useful reagents and methods for a variety of therapeutic, diagnostic, agricultural, target validation, genomic discovery, genetic engineering, and pharmacogenomic applications.

In one particular embodiment, the mNS molecules of the present invention comprise a stem-loop (hairpin) structure, wherein the stem contains a double stranded nucleic acid (dsNA) sequence capable of being cleaved by dicer and releasing at least one small interfering nucleic acid (siNA) that is capable of suppressing an mRNA through the RNAi pathway. In addition, the loop of the mNS molecule contains at least one antisense nucleic acid (asNA). Generally such molecules will be referred to herein as hairpin-forming nucleic acids with loop antisense or "hp NAas."

The siNA and the asNA of the hpNAas may target the same location in the same gene and/or mRNA. In a further example embodiment the siNA and the asNA of the hpNAas may target a different location in the same gene and/or mRNA. The siNA and the asNA of the hpNAas may also target different genes and/or mRNAs.

The stem portion of the hpNAas may contain more than one sequence capable of generating an siNA. If there is more than one siNA generated from the stem of the hpNAas, these siNAs may target the same site on the same mRNA. The siNAs may target different sites on the same mRNA. The siNAs may also target different mRNAs.

The loop portion of the hpNAas may contain more than one asNA sequence. If there is more than one asNA in the loop of the hpNAas, these asNAs may target the same site on the same gene and/or mRNA. The asNAs may target different sites on the same gene and/or mRNA. The asNAs may also target different genes and/or mRNAs.

In a further example embodiment of the present invention, the stem portion of the hpNAas may contain more then one sequence capable of generating an siNA and the loop portion of the hpNAas may contain more than one asNA sequence. These siNAs and asNAs may target the same site on the same mRNA, different sites on the same mRNA, different mRNAs, or any combination thereof.

In one particular embodiment, a single siNA and/or asNA from an hpNAas of the present invention may target more than one gene, nucleotide sequence, and/or protein. Because many genes may share some degree of sequence homology with each other, siNA and/or asNA molecules may be designed to target a class of genes (and associated receptor or ligand genes) or, alternatively, specific genes by selecting sequences that are either shared amongst different gene targets or alternatively that are unique for a specific gene target. In one example embodiment, the siNA and/or asNA molecule may be designed to target conserved regions of, for example, an RNA sequence having homology between several genes so as to target several genes or gene families (e.g., different gene isoforms, splice variants, mutant genes etc.) with one siNA and/or asNA molecule. In another example embodiment, the siNA and/or asNA molecule may be designed to target a sequence that is unique to a specific gene, nucleotide sequence, and/or protein due to the high degree of specificity that the siNA and/or asNA molecule requires to mediate a modulating activity.

In a further example embodiment of the present invention, the hpNAas molecules may contain one or more splice site(s). These splice sites may be operationally placed and oriented so as to allow the cleavage of the loop portion of the hpNAas from the stem portion of the hpHAas as though it were an intron. hpNAas containing such operationally oriented placed splices sites will hereinafter be referred to as "intron containing hpNAas" or "ihpNAas."

In another embodiment, mNS may contain a gene of interest operably linked to a promoter. Where the mNS contains a hairpin or a loop, particular embodiments of the present invention allow for the presence of the promoter and gene of interest within the loop. In other embodiments, the asNA may be present or absent in the loop containing the promoter and gene of interest.

The gene of interest may be any gene that a user wishes to express. The gene may be the same or related to the target of the mNS. By way of non-limiting example, the mNS could target a mutated form of a gene of interest while at the same time providing a normal or engineered copy as a replacement. In a further example embodiment, the promoter and gene of interest may be placed near or within one or more sequence(s) that will promote integration into a genome. Examples of promoters useful in the present invention include, but are not limited to, viral, retroviral, mammalian, plant, bacterial, constitutive, regulatable, fungal, yeast, algal, and insect promoters. Plant promoters useful in the present invention include, for example, those identified in *Arabidopsis*, sunflower, cotton, rapeseed (including canola), maize, wheat, castor, palm, tobacco, peanut, sorghum, sugarcane, or soybean. Suitable promoters useful in the present invention include, for example, seed-specific promoters, inducible promoters, constitutive promoters, including but not limited to, 2S-storage protein, phaseolin, CaMV 35S, napin, cruciferin, ubiquitin, oleosin, cassava vein mosaic virus, prunin, legumin, and octopine synthase.

The introduction of chemically modified or synthetic nucleotides and/or sugars into mNS molecules can provide a powerful tool in overcoming potential limitations of in vivo stability and bioavailability inherent to native RNA molecules that are delivered exogenously. For example, the use of chemically modified mNS or mNS-containing synthetic nucleotides may enable a lower dose of a particular mNS for a given therapeutic effect since these molecules tend to have a longer half-life in serum. Furthermore, certain chemical modifications may improve the bioavailability of nucleic acid molecules by targeting particular cells or tissues, and/or improving cellular uptake of the nucleic acid molecule. Therefore, even if the activity of a chemically modified or synthetic nucleic acid molecule is reduced as compared to a native nucleic acid molecule (e.g., when compared to an all RNA nucleic acid molecule), the overall activity of the modified or synthetic nucleic acid molecule may be greater than the native molecule due to improved stability and/or delivery of the molecule. Unlike native unmodified siRNA, chemically modified siNA may also minimize the possibility of activating interferon activity in humans.

In one representative embodiment, a mNS may comprise one or more modifications and/or synthetic bases. Examples of modifications and/or synthetic bases include, but are not limited to, 2'-amino, 2'-O-methyl, 2'-deoxy-2'-fluoro, 2'-deoxy, 2'-methoxyethyl, 4'-thio, 5-C-methyl, "universal base," locked nucleic acid (LNA), morpholino, and "acyclic nucleotides" as well as nucleotides containing a 2'-O or 4'-C methylene bridge, terminal glyceryl and/or inverted deoxy abasic residue incorporation, phosphorothioate internucleotide linkages, and nucleotides having a Northern conformation (e.g., Northern pseudorotation cycle, see, for example, Saenger, *Principles of Nucleic Acid Structure*, Springer-Verlag ed., 1984). The mNS may further comprise one or more deoxyribonucleotides and/or dideoxyribonucleotides.

The term "universal base" as used herein refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see, for example, Loakes, 2001, *Nucleic Acids Research* 29, 2437-2447). The term "acyclic nucleotide" as used herein refers to any nucleotide having an acyclic ribose sugar, for example where any of the ribose carbons (C1, C2, C3, C4, or C5), are independently or in combination absent from the nucleotide.

Bases in a mNS can be modified by, for example, the addition of substituents at, or modification of one or more positions, for example, on the pyrimidines and purines. The addition of substituents may or may not saturate a double bond, for example, of the pyrimidines and purines. Examples of substituents include, but are not limited to, alkyl groups, nitro groups, halogens, and/or hydrogens. The alkyl groups may be of any length, preferably from one to six carbons. The alkyl groups may be saturated or unsaturated; and may be straight-chained, branched or cyclic. The halogens may be any of the halogens including, but not limited to, bromine, iodine, fluorine, and/or chlorine.

Further modification of the bases may be accomplished by the interchanging and/or substitution of the atoms in the bases. Non-limiting examples include: interchanging the positions of a nitrogen atom and a carbon atom in the bases, substituting a nitrogen and/or a silicon atom for a carbon atom, substituting an oxygen atom for a sulfur atom, and/or substituting a nitrogen atom for an oxygen atom. Other modifications of the bases include, but are not limited to, the fusing of an additional ring to the bases, such as an additional five- or six-membered ring. The fused ring may carry various further groups.

Specific examples of modified bases include, but are not limited to, 2,6-diaminopurine, 2-aminopurine, pseudoisocytosine, E-base, thiouracil, ribothymidine, dihydrouridine, pseudouridine, 4-thiouridine, 3-methylcytidine, 5-methylcytidine, $N^6$-methyladenosine, $N^6$-isopentenyladenosine, -methylguanosine, queuosine, wyosine, etheno-adenine, etheno-cytosine, 5-methylcytosine, bromothymine, azaadenine, azaguanine, 2'-fluoro-uridine, and 2'-fluoro-cytidine.

mNS may comprise modified and/or synthetic nucleotides as a percentage of the total number of nucleotides present in the mNS molecule. As such, a mNS molecule of the invention may generally comprise modified and/or synthetic nucleotides from about 5% to about 100% of the nucleotide positions (e.g., 5%, 10%, 15%, 20%, 25%, 30%, 35%, 40%, 45%, 50%, 55%, 60%, 65%, 70%, 75%, 80%, 85%, 90%, 95% or 100% of the nucleotide positions). The actual percentage of modified nucleotides present in a given mNS molecule depends on the total number of nucleotides present in the mNS.

In a particular embodiment, mNS of the present invention comprises a molecular backbone attaching the various nucleotides in sequence. Example embodiments of mNS may have molecular backbones including, but not limited to, ribose, 2'-O-alkyl ribose, 2'-O-methyl ribose, 2'-O-allyl ribose, deoxyribose, 2-deoxyribose, morpholino, and/or peptide backbones. The backbone may comprise sugar and/or non-sugar units. These units may be joined together by any manner known in the art. The nucleotides may be joined by linking groups. Some examples of linking groups include, but not limited to, phosphate, thiophosphate, dithiophosphate, methylphosphate, amidate, phosphorothioate, methylphosphonate, phosphorodithioate, and/or phosphorodiamidate groups. Alternatively, the nucleotides may be joined directly together.

A sugar backbone may comprise any naturally occurring sugar. Examples of naturally occurring sugars include, but are not limited to, ribose, deoxyribose, and/or 2-deoxyribose. Sugar units of a backbone may be modified such that the modified sugar backbone is resistant to cleavage. The sugars of a backbone may be modified by methods known in the art, for example, to achieve resistance to nuclease cleavage. Examples of modified sugars include, but are not limited to, 2'-O-alkyl riboses, such as 2'-O-methyl ribose, and 2'-O-allyl ribose. The sugar units may be joined by phosphate linkers. Typical sugar units of the invention may be linked to each other by 3'-5', 3'-3', or 5'-5' linkages. Additionally, 2'-5' linkages are also possible if the 2' OH is not otherwise modified.

A non-sugar backbone may comprise any non-sugar molecule to which bases may be attached. Non-sugar backbones are known in the art. Examples include, but are not limited to, morpholino and peptide nucleic acids (PNAs). A morpholino backbone is made up of morpholino rings (tetrahydro-1,4-oxazine) and may be joined by non-ionic phosphorodiamidate groups. Modified morpholinos known in the art may be used in the present invention.

PNAs result when bases are attached to an amino acid backbone by molecular linkages. Examples of such linkages include, but are not limited to, methylene carbonyl, ethylene carbonyl, and ethyl linkages. The amino acids may be any amino acid, natural or non-natural, modified or unmodified, and are preferably alpha amino acids. The amino acids may be identical or different from one another. One non-limiting example of a suitable amino acid includes an amino alkyl-amino acid, such as (2-aminoethyl)-amino acid.

Examples of PNAs include, but are not limited to, N-(2-aminoethyl)-glycine, cyclohexyl PNA, retro-inverso, phosphone, propinyl, and aminoproline-PNA. PNAs may be chemically synthesized by methods known in the art. Examples include, but are not limited to, modified Fmoc and/or tBoc peptide synthesis protocols.

In addition to the above mentioned uniform antisense oligonucleotides, it is apparent to one of skill in the art that multiple types of backbone may be mixed in a single mNS molecule. For example, a single mNS molecule may contain one or more 2'-O-methyl nucleotides, one or more morpholinos, one or more RNA nucleotides, and one or more PNAs.

In example embodiments where the mNS of the present invention includes a hpANas, the length of the siNA and/or asNA in an hpANas is not critical, so long as the length is sufficient to hybridize specifically to the target. For example, the base paring segment may have from about two to about 100 bases, from about 10 to 50 bases, about 25 bases, or any individual number between about 10 and about 75 bases.

Various factors may be considered when determining the length of the siNA and/or asNA segments, such as target specificity, binding stability, cellular transport and/or in vivo delivery. siNA and/or asNA segments should be long enough to stably bind to the target of interest. Also, the siNA and/or asNA segments should be long enough to allow for reasonable binding specificity as a shorter sequence has a higher probability of occurring elsewhere in the genome than a longer sequence. Further considerations related to the length of an siNA and/or asNA segments include, the efficiency of in vivo or ex vivo delivery, stability of the siNA and/or asNA segments in vivo or in vitro, and/or the stability of the target of interest bound or unbound by an siNA and/or asNA segment.

In a further example embodiment, a mNS molecule may be modified to optimize their use in various applications. Optimization may include, but is not limited to, one or more modifications to improve delivery, cellular uptake, intracellular localization, and/or pharmacokinetics. One manner in which an mNS molecule may be modified is by the addition of specific signal sequences. Examples include, but are not limited to, nuclear retention signals, nuclear localization signals, and/or sequences that promote transport across cell membranes, the blood brain barrier, and/or the placental barrier. Specific examples include, but are not limited to, polylysine, poly(E-K), the SV40 T antigen nuclear localization signal, the N-terminus of HIV-TAT protein, peptides derived from the *Drosophila Antennapedia* protein, a transdermal delivery peptide such as, for example, those described by Chen et al., *Nature Biotechnology* 24:4 455-460, and/or the Dowdy Tat peptide. Sequences which localize antisense oligonucleotides to specific cell types are also contemplated. In one embodiment, the invention features an active ingredient comprising a mNS molecule of the invention.

In a further example embodiment a mNS may be combined with one or more carriers, adjuvants, and/or diluents to form a medicament or chemical treatment for a living organism. Examples of such carriers, adjuvants, and/or diluents include, but are not limited to, water, saline, Ringer's solution, cholesterol and/or cholesterol derivatives, liposomes, lipofectin, lipofectamine, lipid anchored polyethylene glycol, block copolymer F108, and/or phosphatides, such as dioleooxyphosphatidylethanolamine, phophatidyl choline, phophatidylgylcerol, alpha-tocopherol, and/or cyclosporine. In many cases the mNS molecules may be mixed with one or more carriers, adjuvants, and/or diluents to form a dispersed composition or medicament which may be used to treat a disease, infection, or condition. See, e.g., *Remington's Pharmaceutical Sciences*; Goodman and Gilman's *The Pharmacologic Basis of Therapeutics; Current Protocols in Molecular Biology*. It would be apparent to a person of ordinary skill in the art that such a dispersed composition may also be used to disrupt the proper expression of genes, nucleotide sequences and/or proteins involved in disease or infective processes, or in production of animal or plant products. For example, the composition may be used to produce a plant with increased levels of a product of a fatty acid synthesis or lipid metabolism gene.

mNS molecules, with or without an adjuvant and/or a carrier, may be administered to an organism or subject in any manner that will allow the mNS molecules to modulate expression of a target. Examples include, but are not limited to, site-specific injection, systemic injection, and/or administration intravenously, orally, and/or topically. Organisms and subjects contemplated by the invention include, but are not limited to, bacteria, cells, cell culture systems, plants, fungi, animals, nematodes, insects, and/or mammals, such as humans. Plants contemplated by the invention include, for example, *Arabidopsis*, sunflower, cotton, rapeseed (including canola), maize, wheat, castor, palm, tobacco, peanut, sorghum, sugarcane, and soybean.

The target may be, for example, a nucleic acid that may be an endogenous gene, an exogenous gene, a viral nucleic acid, or RNA, such as a mammalian gene, plant gene, viral gene, fungal gene, bacterial gene, plant viral gene, or mammalian viral gene. Examples of mammalian viruses include, but are not limited to, hepatitis C virus, human immunodeficiency virus, hepatitis B virus, herpes simplex virus, cytomegalovirus, human papilloma virus, respiratory syncytial virus, influenza virus, and severe acute respiratory syndrome virus (SARS).

As will be apparent to one of ordinary skill in the art, a target may also be a nucleotide sequence or protein. As will also be understood, the mNS molecules of the invention do not tend to alter the protein itself, but rather target the molecules that control the generation of that protein. Examples of proteins include, but are not limited to, endogenous protein, an exogenous protein, a mammalian protein, plant protein, viral protein, fungal protein, bacterial protein, plant viral protein, or mammalian viral protein. Examples of nucleotide sequences include, but are not limited to, DNA, RNA, and PNA sequences.

In one example embodiment, a mNS molecule of the invention comprises a sense region and an antisense region, wherein the sense region includes a terminal cap moiety at the 5'-end, the 3'-end, or both of the 5' and 3' ends. The cap moiety may be an inverted deoxy abasic moiety, an inverted deoxy thymidine moiety, or a thymidine moiety.

One particular embodiment of the invention provides a vector comprising a nucleic acid sequence encoding at least one mNS molecule of the invention in a manner that allows expression of the nucleic acid molecule. Examples of vectors include, but are not limited to, plasmids, cosmids, retroviral vectors, agrobacterium, viral vectors, bacterial vectors, yeast vectors, eukaryotic vectors, plant vectors, and mammalian vectors. Other embodiments of the invention provide mammalian cells, plant cells, or agrobacterium comprising such a vector. The cell may be mammalian in nature, such as, for example, a human cell. The mNS molecule of the vector may comprise a sense region, an antisense region, an antisense sequence, and/or a gene.

In one embodiment, the mNS molecules of the present invention feature a chemically modified short interfering nucleic acid molecule (siNA) capable of mediating RNA interference (RNAi) inside a cell or reconstituted in vitro system, wherein the chemical modification comprises a conjugate attached to the chemically modified siNA molecule. The conjugate may be attached to the chemically modified siNA molecule via a covalent attachment. In a specific embodiment, the conjugate is attached to the chemically modified siNA molecule via a biodegradable linker. The conjugate molecule can be attached at the 3'-end of either the sense strand, the antisense strand, or both strands of the chemically modified siNA molecule. The conjugate molecule can be attached at the 5'-end of either the sense strand, the antisense strand, or both strands of the chemically modified siNA molecule. The conjugate molecule can also be attached both at the 3'-end and 5'-end of either the sense strand, the antisense strand, or both strands of the chemically modified siNA molecule, or any combination thereof. The conjugate molecule of the invention can comprise a molecule that facilitates delivery of a chemically modified siNA molecule into a biological system, such as a cell. In a particular embodiment, the conjugate molecule attached to the chemically modified siNA molecule is a poly ethylene glycol, human serum albumin, or a ligand for a cellular receptor that may mediate cellular uptake. Examples of specific conjugate molecules contemplated by the instant invention that can be attached to chemically modified siNA molecules are described in Vargeese et al., U.S. Ser. No. 10/201,394, the contents of which are incorporated by reference herein. The type of conjugates used and the extent of conjugation of siNA molecules of the invention may be evaluated for improved pharmacokinetic profiles, bioavailability, and/or stability of siNA constructs, while at the same time maintaining the ability of the siNA to mediate RNAi activity. As such, one skilled in the art may screen siNA constructs that are modified with various conjugates to determine whether the siNA conjugate complex possesses improved properties while maintaining the ability to mediate RNAi, such as, for example, in animal models that are generally known in the art.

In another embodiment, the invention features a method for modulating the expression of a gene within a cell. The method includes synthesizing a mNS molecule of the invention, which may be chemically modified, wherein the mNS molecule comprises a sequence complementary to RNA of the gene. The mNS molecule can include a sequence substantially similar to the sequence of the target RNA. The mNS molecule can then be introduced into a cell under conditions suitable to modulate the expression of the gene in the cell.

In another example embodiment, the invention features a method for modulating the expression of more than one gene within a cell. The method includes synthesizing a mNS molecule of the invention, which may be chemically modified, wherein the mNS molecule comprises a sequence complementary to RNA of the genes. The mNS molecule can then be introduced into a cell under conditions suitable to modulate the expression of the genes in the cell.

In another example embodiment, the invention features a method for modulating the expression of more than one gene within a cell. The method includes synthesizing a mNS molecule of the invention, which may be chemically modified, wherein the mNS molecule comprises a sequence complementary to RNA of the gene and wherein the mNS molecule comprises a sequence substantially similar to the sequence of the target RNA. The mNS molecule can then be introduced into a cell under conditions suitable to modulate the expression of the genes in the cell.

In a particular embodiment, mNS molecules of the invention are used as reagents in ex vivo applications. For example, mNS molecules can be introduced into tissue or cells that are transplanted into an organism or subject for therapeutic effect. The cells and/or tissue may be derived from an organism or subject that later receives the explant. Alternatively, the cells and/or tissue may be derived from another organism or subject prior to transplantation. The mNS molecules may be used to modulate the expression of one or more genes in the cells or tissue, such that the cells or tissue obtain a desired phenotype and are able to perform a function when transplanted in vivo. In one example embodiment, certain target cells from an organism or subject are extracted. These extracted cells are contacted with mNS molecules targeting a specific nucleotide sequence within the cells under conditions suitable for uptake of the mNS molecules by these cells (e.g., using delivery reagents such as cationic lipids, liposomes and the like, or using techniques such as electroporation to facilitate the delivery of mNS molecules into cells). The cells are then reintroduced back into the same organism or other organisms. Non-limiting examples of ex vivo applications include use in organ/tissue transplant, tissue grafting, or in treatment of pulmonary disease (e.g., restenosis), or to prevent neointimal hyperplasia and atherosclerosis in vein grafts. Such ex vivo applications may also used to treat conditions associated with coronary and peripheral bypass graft failure, for example, such methods may be used in conjunction with peripheral vascular bypass graft surgery and coronary artery bypass graft surgery. Additional applications include use in transplants to treat CNS lesions or injury, including use in treatment of neurodegenerative conditions such as Alzheimer's disease, Parkinson's disease, Epilepsy, Dementia, Huntington's disease, or amyotrophic lateral sclerosis (ALS).

In yet another embodiment, the invention features a method of modulating the expression of a gene in an organism. The method includes synthesizing a mNS molecule of the invention, wherein the mNS molecule comprises a sequence complementary to RNA of the gene. The mNS molecule can then be introduced into the organism under conditions suitable to modulate the expression of the gene in the organism.

In another example embodiment, the invention features a method of modulating the expression of more than one gene in an organism. The method includes synthesizing a mNS molecule of the invention, wherein the mNS molecule comprises a sequence complementary to RNA of the genes. The mNS molecule can then be introduced into the organism under conditions suitable to modulate the expression of the genes in the organism. In an alternative embodiment, the invention features a method for modulating the expression of a gene within a cell by synthesizing a mNS molecule of the invention, wherein the mNS molecule comprises a sequence having complementarity to RNA of the gene. The mNS molecule can then be introduced into a cell under conditions suitable to modulate the expression of the gene in the cell.

In other embodiments, the invention features a method for modulating the expression of more than one gene within a cell, which includes synthesizing mNS molecules of the invention, wherein the mNS molecule comprises a sequence having complementarity to RNA of the genes. The mNS molecule can then be contacted with a cell in vitro or in vivo under conditions suitable to modulate the expression of the genes in the cell. In another embodiment, the invention includes a method of modulating the expression of a gene in an organism. A mNS molecule having complementarity to RNA of the gene can be synthesized and the mNS molecule can be introduced into the organism under conditions suitable to modulate the expression of the gene in the organism. Another embodiment features a method of modulating the expression of more than one gene in an organism by synthesizing mNS molecules that include a sequence having complementarity to RNA of the genes and introducing the mNS molecules into the organism under conditions suitable to modulate the expression of the genes in the organism. Another embodiment includes a method of modulating the expression of a gene in an organism by contacting the organism with the mNS molecule of the invention under conditions suitable to modulate the expression of the gene in the organism. Yet another alternative embodiment features a method of modulating the expression of more than one gene in an organism by contacting the organism with one or more mNS molecules of the invention under conditions suitable to modulate the expression of the genes in the organism.

The mNS molecules of the invention may be designed to inhibit target gene expression through RNAi targeting of a variety of RNA molecules. In one embodiment, the mNS molecules of the invention can be used to target various RNAs corresponding to a target gene. Non-limiting examples of such RNAs include messenger RNA (mRNA), alternate RNA splice variants of target gene(s), post-transcriptionally modified RNA of target gene(s), pre-mRNA of target gene(s), and/or RNA templates. If alternate splicing produces a family of transcripts that are distinguished by usage of appropriate exons, the instant invention may be used to inhibit gene expression through the appropriate exons to specifically inhibit or to distinguish among the functions of gene family members. For example, a protein that contains an alternatively spliced transmembrane domain may be expressed in both membrane-bound and secreted forms. Use of the invention to target the exon containing the transmembrane domain may be used to determine the functional consequences of pharmaceutical targeting of membrane bound, as opposed to the secreted form of the protein. Non-limiting examples of applications of the invention relating to targeting these RNA molecules include therapeutic pharmaceutical applications, molecular and pharmaceutical discovery applications, modification of animal and plant products/molecules, molecular diagnostic and gene function applications, and gene mapping, for example, using single nucleotide polymorphism mapping with siNA molecules of the invention. Such applications may be implemented using known gene sequences or from partial sequences available from an expressed sequence tag (EST). In one embodiment of the invention, the modification involves a fatty acid synthesis gene or a lipid metabolism gene in a plant.

In another embodiment, the mNS molecules of the invention can be used to target conserved sequences corresponding to a gene family or gene families. As such, mNS molecules targeting multiple gene targets may provide increased biological effect or a modified effect (such as in the production of fatty acid synthesis in a plant or a seed). In addition, mNS molecules may be used to characterize pathways of gene function in a variety of applications. For example, the present invention may be used to inhibit the activity of target gene(s) in a pathway to determine the function of uncharacterized gene(s) in gene function analysis, mRNA function analysis, or translational analysis. The invention may be used to determine potential target gene pathways involved in various diseases and conditions toward product, molecule, or pharmaceutical development. The invention may be used to understand pathways of gene expression involved in, for example, development, such as prenatal development and postnatal development, and/or the progression and/or maintenance of cancer, infectious disease, autoimmunity, inflammation, endocrine disorders, renal disease, pulmonary disease, cardiovascular disease, birth defects, ageing, any other disease or condition related to gene expression. The invention may be used to modify expression of genes in plants or animals, or may be used to modify synthesis of animal or plant products, such as, for example, modification of fatty acid synthesis in plants and plant seeds.

In another embodiment, the invention features a method for validating a target gene. The method includes synthesizing a mNS molecule of the invention, which may be chemically modified and further include a sequence complementary to RNA of a target gene. The mNS molecule can then be introduced into a biological system under conditions suitable for modulating expression of the target gene in the biological system. The function of the gene can then be determined by assaying for any phenotypic change in the biological system.

By "biological system" is meant material, in a purified or unpurified form, from biological sources, including but not limited to human, animal, plant, insect, bacterial, viral or other sources, wherein the system comprises the components required for RNAi activity. The term "biological system" includes, for example, a cell, tissue, or organism, or extract thereof. The term "biological system" also includes reconstituted RNAi systems that may be used in an in vitro setting.

By "phenotypic change" is meant any detectable change to a cell that occurs in response to contact or treatment with a nucleic acid molecule of the invention (e.g., mNS). Such detectable changes include, but are not limited to, changes in shape, size, proliferation, motility, protein expression or RNA expression or other physical or chemical changes as may be assayed by methods known in the art. The detectable change may also include expression of reporter genes/molecules such as Green Florescent Protein (GFP) or various tags that are used to identify an expressed protein or any other cellular component that may be assayed.

In a particular embodiment, the invention features a kit containing a mNS molecule of the invention, which may be used to modulate the expression of a target in a cell, tissue, or organism. In another embodiment, the invention features a kit containing more than one mNS molecule of the invention, which may be chemically modified, that may be used to modulate the expression of more than one target gene in a cell, tissue, or organism. In yet another embodiment, the invention features a kit containing a vector encoding a mNS molecule of the invention that may be used to modulate the expression of a gene in a biological system. In another embodiment, the invention features a kit containing a vector encoding more than one mNS molecule of the invention that may be used to modulate the expression of more than one target gene in a biological system.

Another embodiment of the invention features a cell containing one or more mNS molecules of the invention. In one particular embodiment, there is provided a cell containing a vector encoding one or more mNS molecules of the invention. The cell containing a mNS molecule of the invention can be a mammalian cell or a plant cell. For example, cells containing a mNS molecule can be from *Arabidopsis*, sunflower, cotton, rapeseed (including canola), maize, wheat, castor, palm, tobacco, peanut, sorghum, sugarcane, or soybean.

The invention also includes mNS molecules that mediate RNAi in a cell or reconstituted system, wherein the mNS molecule comprises one or more chemical modifications described herein that modulate the polymerase activity of a cellular polymerase capable of generating additional endogenous siRNA molecules having sequence homology to the chemically modified mNS molecule.

The invention also includes a mNS molecule that mediates RNAi in a cell or reconstituted system, wherein the mNS molecule comprises one or more chemical modifications described herein that modulates the cellular uptake of the mNS molecule. In one specific embodiment, the invention features mNS molecule that mediate expression of a target, wherein the mNS molecule comprises one or more chemical modifications described herein that increases the bioavailability of the mNS molecule, for example, by attaching polymeric conjugates such as polyethyleneglycol or equivalent conjugates that improve the pharmacokinetics of the mNS molecule, or by attaching conjugates that target specific tissue types or cell types in vivo. Non-limiting examples of such conjugates are described in Vargeese et al., U.S. Ser. No. 10/201,394 incorporated by reference herein.

In one example embodiment, the invention features a method for generating mNS molecule of the invention with improved bioavailability, comprising (a) introducing a conjugate into the structure of a mNS molecule, and (b) assaying the mNS molecule of step (a) under conditions suitable for isolating mNS molecule having improved bioavailability. Such conjugates may include ligands for cellular receptors, such as peptides derived from naturally occurring protein ligands; protein localization sequences, including cellular ZIP code sequences; antibodies; nucleic acid aptamers; vitamins and other co-factors, such as folate and N-acetylgalactosamine; polymers, such as polyethyleneglycol (PEG); phospholipids; cholesterol; polyamines, such as spennine or spermidine; and others. In another embodiment, polyethylene glycol (PEG) may be covalently attached to mNS molecule of the present invention. The attached PEG may be any molecular weight, preferably from about 2,000 to about 50,000 daltons (Da).

The present invention may be used alone or as a component of a kit having at least one of the reagents necessary to carry out the in vitro or in vivo introduction of RNA to test samples and/or subjects. For example, suitable components of the kit can include a mNS molecule of the invention and a vehicle that promotes introduction of the mNS molecule into cells of interest as described herein (e.g., using lipids and other methods of transfection known in the art, see for example Beigelman et al., U.S. Pat. No. 6,395,713). The kit may be used for target validation, such as in determining gene function and/or activity, or in drug optimization, and in drug discovery (see for example Usman et al., U.S. Ser. No. 60/402,996). Such a kit may also include instructions to allow a user of the kit to practice the invention.

The term "short interfering nucleic acid," "siNA," "short interfering RNA," "siRNA," "short interfering nucleic acid molecule," "short interfering oligonucleotide molecule," or "chemically modified short interfering nucleic acid molecule" as used herein refers to any nucleic acid molecule capable of inhibiting or down regulating gene expression or viral replication, for example by mediating RNA interference "RNAi" or gene silencing in a sequence-specific manner; see for example Bass, 2001, *Nature* 411, 428-429; Elbashir et al., 2001, *Nature* 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, *Science* 297, 1818-1819; Volpe et al., 2002, *Science* 297, 1833-1837; Jenuwein, 2002, *Science* 297, 2215-2218; and Hall et al., 2002, *Science* 297, 2232-2237; Hutvagner and Zamore, 2002, *Science* 297, 2056-60; McManus et al., 2002, *RNA* 8, 842-850; Reinhart et al., 2002, *Gene & Dev.* 16, 1616-1626; and Reinhart & Bartel, 2002, *Science* 297, 1831). For example, the siNA may be a double-stranded polynucleotide molecule comprising complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof.

The siNA may be assembled from two separate oligonucleotides, where one strand is the sense strand and the other is the antisense strand, and wherein the antisense and sense strands are complementary (i.e., each strand comprises nucleotide sequence that is complementary to nucleotide sequence in the other strand; such as where the antisense strand and sense strand form a duplex or double stranded structure, for example wherein the double stranded region is about 19 base pairs). The antisense strand comprises a nucleotide sequence that is complementary to the nucleotide sequence in a target nucleic acid molecule or a portion thereof, and the sense strand comprises a nucleotide sequence corresponding to the target nucleic acid sequence or a portion thereof. Alternatively, the siNA can be assembled from a single oligonucleotide, where the complementary sense and antisense regions of the siNA are linked by means of a nucleic acid based or non-nucleic acid-based linker(s). The siNA may be a polynucleotide with a duplex, asymmetric duplex, hairpin or asymmetric hairpin secondary structure, having complementary sense and antisense regions, wherein the antisense region comprises nucleotide sequence that is complementary to nucleotide sequence in a separate target nucleic acid molecule or a portion thereof, and the sense region having nucleotide sequence corresponding to the target nucleic acid sequence or a portion thereof. The siNA may be a circular single-stranded polynucleotide having two or more loop structures and a stem comprising complementary sense and antisense regions, wherein the antisense region comprises nucleotide sequence that is complementary to a nucleotide sequence in a target nucleic acid molecule or a portion thereof, and the sense region having nucleotide sequence corresponding to the target nucleic acid sequence or a portion thereof. The circular polynucleotide may be processed either in vivo or in vitro to generate an active siNA molecule capable of mediating RNAi. The siNA may also comprise a single stranded polynucleotide having nucleotide sequence complementary to nucleotide sequence in a target nucleic acid molecule or a portion thereof (e.g., where such siNA molecule does not require the presence within the siNA molecule of nucleotide sequence corresponding to the target nucleic acid sequence or a portion thereof). The single stranded polynucleotide may further comprise a terminal phosphate group, such as a 5'-phosphate (see, e.g., Martinez et al., 2002, *Cell.* 110, 563-574, and Schwarz et al., 2002, *Molecular Cell* 10, 537-568), or 5',3'-diphosphate.

In certain embodiments, the siNA molecule of the invention can include separate sense and antisense sequences or regions, wherein the sense and antisense regions are covalently linked by nucleotide or non-nucleotide linker molecules as are known in the art. Alternatively, the sense and antisense regions can be non-covalently linked by ionic interactions, hydrogen bonding, van der Waals interactions, hydrophobic interactions, and/or stacking interactions. In certain embodiments, the siNA molecules of the invention comprise a nucleotide sequence that is complementary to the nucleotide sequence of a target gene. The siNA molecule of the invention can interact with the nucleotide sequence of a target gene in a manner that causes inhibition of expression of the target gene. The siNA molecules of the present invention need not be limited to those molecules containing only RNA, but may further encompass chemically modified nucleotides and non-nucleotides. In certain embodiments, the short interfering nucleic acid molecules of the invention lack 2'-hydroxy (2'-OH) containing nucleotides. Particular embodiments include short interfering nucleic acids that do not require the presence of nucleotides having a 2'-hydroxy group for mediating RNAi and, as such, short interfering nucleic acid molecules of the invention optionally do not include any ribonucleotides (i.e., nucleotides having a 2'-OH group). Such siNA molecules that do not require the presence of ribonucleotides within the siNA molecule to support RNAi may, however, have one or more attached linker(s) or other attached or associated groups, moieties, or chains containing one or more nucleotides with 2'-OH groups. Optionally, siNA molecules may comprise ribonucleotides at about 5, 10, 20, 30, 40, or 50% of the nucleotide positions.

The modified short interfering nucleic acid molecules of the invention may also be referred to as short interfering modified oligonucleotides "siMON." As used herein, the term "siNA" is equivalent to other terms used to describe nucleic acid molecules that are capable of mediating sequence specific RNAi, such as, for example, short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA). In addition, as used herein, the term "RNAi" is equivalent to other terms used to describe sequence specific RNA interference, such as post transcriptional gene silencing, translational inhibition, or epigenetics. For example, siNA molecules of the invention may be used to epigenetically silence genes at both the post-transcriptional level and the pre-transcriptional level. By way of non-limiting example, epigenetic regulation of gene expression by siNA molecules of the invention may result from siNA mediated modification of chromatin structure to alter gene expression (see, for example, Allshire, 2002, *Science* 297, 1818-1819; Volpe et al., 2002, *Science* 297, 1833-1837; Jenuwein, 2002, *Science* 297, 2215-2218; and Hall et al., 2002, *Science* 297, 2232-2237).

The term "asymmetric hairpin" means a linear siNA molecule comprising an antisense region, a loop portion that may comprise nucleotides or non-nucleotides, and a sense region that comprises fewer nucleotides than the antisense region (to the extent that the sense region has enough complementary nucleotides to base pair with the antisense region and form a duplex with loop). For example, an asymmetric hairpin siNA molecule of the invention may comprise an antisense region having a length sufficient to mediate RNAi in a cell or in vitro system (e.g., about 19 to about 22 nucleotides) and a loop region comprising about four to about eight nucleotides, and a sense region having about three to about 18 nucleotides that are complementary to the antisense region. The asymmetric hairpin siNA molecule may also comprise a 5'-terminal phosphate group that may be chemically modified. The loop portion of the asymmetric hairpin siNA molecule may comprise nucleotides, non-nucleotides, linker molecules, or conjugate molecules as described herein.

The term "modulate" means that the expression of the gene, or level of RNA molecule or equivalent RNA molecules encoding one or more proteins or protein subunits, or activity or level of one or more proteins or protein subunits, is up regulated or down regulated, such that expression, level, or activity is greater than or less than that observed in the absence of the modulator. For example, the term "modulate" may mean "inhibit," but is not limited to this definition.

The terms "inhibit," "down-regulate," or "reduce," mean that the expression of the gene, or level of RNA molecules or equivalent RNA molecules encoding one or more proteins or protein subunits, or activity of one or more proteins or protein subunits, is reduced below that observed in the absence of the mNS molecules of the invention. In a particular embodiment, inhibition, down-regulation, or reduction with a mNS molecule results in a level that is below the level observed in the presence of an inactive or attenuated molecule. Likewise, inhibition, down-regulation, or reduction with mNS molecules results in a level that is below the level observed in the presence of, for example, a mNS molecule with scrambled sequence or with mismatches. In another example, inhibition, down-regulation, or reduction of gene expression with a nucleic acid molecule of the instant invention is greater in the presence of the nucleic acid molecule than in its absence.

By "gene" or "target gene" is meant, a nucleic acid that encodes an RNA, for example, nucleic acid sequences including, but not limited to, structural genes encoding a polypeptide. The target gene may be a gene derived from a cell, an endogenous gene, a transgene, or exogenous genes, such as genes of a pathogen (e.g., a virus), which is present in the cell after infection. The cell containing the target gene may be derived from or contained in any organism, such as a plant, animal, protozoan, virus, bacterium, or fungus. Non-limiting examples of plants include monocots, dicots, or gymnosperms, and more specifically, *Arabidopsis*, sunflower, cotton, rapeseed, maize, palm, tobacco, peanut or soybean. Non-limiting examples of animals include vertebrates or invertebrates. Non-limiting examples of fungi include molds or yeasts.

"Highly conserved sequence region" means a nucleotide sequence of one or more regions in a target gene that does not vary significantly from one generation to the other or from one biological system to the other.

"Sense region" means a nucleotide sequence of a siNA molecule having complementarity to an antisense region of the siNA molecule. The sense region of a siNA molecule may comprise a nucleic acid sequence having homology (i.e., sequence identity or partial identity) with a target nucleic acid sequence.

"Antisense region" means a nucleotide sequence of a siNA molecule having complementarity to a target nucleic acid sequence. In addition, the antisense region of a siNA molecule may optionally comprise a nucleic acid sequence having complementarity to a sense region of the siNA molecule.

"Target nucleic acid" means any nucleic acid sequence whose expression or activity is to be modulated. The target nucleic acid may be DNA or RNA, such as endogenous DNA or RNA, viral DNA or viral RNA, or other RNA encoded by a gene of a virus, bacteria, fungus, animal, or plant.

As referred to in this application, "treating" or "treatment" does not require a complete alteration of a phenotype. It means that the symptoms of the underlying condition are at least reduced, and/or that one or more of the underlying cellular, physiological, or biochemical causes or mechanisms causing the symptoms are reduced and/or eliminated. It is understood that reduced, as used in this context, means relative to the state of the condition, including the molecular state of the condition, not just the physiological state of the condition.

By "condition" is meant any state in a subject or organism that one might wish to alter. Such a state should be attributable to the expression or lack of expression of a gene, nucleotide sequence and/or protein. Examples of conditions include, but are not limited to, diseases, genetic abnormalities, infections, cancers, mutations, and cosmetic conditions including, but not limited to, alopecia, obesity, and skin wrinkling. A further non-limiting example of a condition is the normal state in a subject. For example, the normal fatty acid production in a plant (e.g., *Arabidopsis*, sunflower, cotton, rapeseed, maize, palm, tobacco, peanut or soybean) is a condition which might be altered using the compositions and methods of the present invention. As such, the term "condition" includes any state which might be altered for scientific, agricultural, medical, and/or personal reasons.

By "complementarity" is meant that a nucleic acid may form hydrogen bond(s) with another nucleic acid sequence by either traditional Watson-Crick, Hoogstein base-pairing, and/or reverse Hoogstein base-pairing or other non-traditional types. In reference to the nucleic molecules of the present invention, the binding free energy for a nucleic acid molecule with its complementary sequence is sufficient to allow the relevant function of the nucleic acid to proceed (e.g., RNAi activity). Determination of binding free energies for nucleic acid molecules is well known in the art (see, e.g., Turner et al., 1987, *CSH Symp. Quant. Biol. LII* pp. 123-133; Frier et al., 1986, *Proc. Nat. Acad. Sci. USA* 83:9373-9377; Turner et al., 1987, *J. Am. Chem. Soc.* 109:3783-3785).

A percent complementarity indicates the percentage of contiguous residues in a nucleic acid molecule that may form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementarity). "Perfect complementarity" means that all the contiguous residues of a nucleic acid sequence will hydrogen bond with the same number of contiguous residues in a second nucleic acid sequence.

The siNA molecules of the invention represent a novel therapeutic approach to a broad spectrum of diseases and conditions, including cancer or cancerous disease, infectious disease, cardiovascular disease, neurological disease, prion disease, inflammatory disease, autoimmune disease, pulmonary disease, renal disease, liver disease, mitochondrial disease, endocrine disease, reproduction related diseases and conditions, animal or plant product synthesis, and any other indications that may respond to the level of an expressed gene product in a cell or organism.

As used herein "cell" is used in its usual biological sense and does not refer to an entire multicellular organism. The cell may be present in an organism (e.g., plants and animals, including mammals). The cell may be prokaryotic (e.g., bacterial cell) or eukaryotic (e.g., mammalian or plant cell). The cell may be of somatic or germ line origin, totipotent or pluripotent, dividing or non-dividing. The cell may also be derived from or may comprise a gamete or embryo, a stem cell, or a fully differentiated cell, such as, for example, from an animal, bacteria, plant, or seed.

The mNS molecules of the invention can be added directly or may be complexed with cationic lipids, packaged within liposomes, or otherwise delivered to target cells or tissues. The nucleic acid or nucleic acid complexes may be locally administered to relevant tissues ex vivo, or in vivo through, for example, injection, gene gun delivery, infusion pump or stent, with or without their incorporation in biopolymers.

In another aspect, the invention provides cells containing one or more mNS molecules of this invention. The one or more mNS molecules may independently be targeted to the same or different sites.

"RNA" means a molecule comprising at least one ribonucleotide residue. By "ribonucleotide" is meant a nucleotide with a hydroxyl group at the 2' position of a β-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations may include addition of non-nucleotide material, such as to the end(s) of the siNA or internally (e.g., at one or more nucleotides of the RNA). Nucleotides in the RNA molecules of the instant invention may also comprise non-standard nucleotides, such as non-naturally occurring nucleotides or chemically synthesized nucleotides or deoxynucleotides. These altered RNAs may be referred to as analogs or as analogs of naturally occurring RNA.

By "subject" is meant an organism, which is a donor or recipient of explanted cells or the cells themselves. "Subject" also refers to an organism to which the nucleic acid molecules of the invention may be administered. A subject may be a plant, plant cells, a mammal, or mammalian cells, including human cells.

Another embodiment of the invention provides a method of producing a plant with modified levels of endogenous component fatty acids. The method includes modulating the levels of a heterologous gene, such as a fatty acid synthesis or lipid metabolism gene. Fatty acid production in plants and seeds can be modified. Representative plants that can be modified through the present invention include, for example, *Arabidopsis*, sunflower, cotton, rapeseed (including canola), maize, wheat, castor, palm, tobacco, peanut, sorghum, sugarcane, and soybean.

The mNS of the instant invention, individually, in combination with other compounds, or in conjunction with other compounds (such as drugs), may be used to treat diseases or conditions discussed herein (e.g., cancers and other proliferative conditions, viral infection, inflammatory disease, autoimmunity, pulmonary disease, renal disease, ocular disease, etc.). For example, to treat a particular disease or condition, the mNS molecules may be administered to a subject or may be administered to other appropriate cells evident to those skilled in the art, individually or in combination with one or more drugs under conditions suitable for the treatment.

In a further example embodiment, the mNS molecules may be used in combination with other known treatments to treat conditions or diseases discussed above. For example, the described molecules could be used in combination with one or more known therapeutic agents to treat a disease or condition. Non-limiting examples of other therapeutic agents that may be readily combined with a mNS molecule of the invention are enzymatic nucleic acid molecules, allosteric nucleic acid molecules, antisense, decoy, or aptamer nucleic acid molecules, antibodies (such as monoclonal antibodies), small molecules, and other organic and/or inorganic compounds including metals, salts and ions.

Computer modeling techniques for use in predicting/ evaluating derivatives of the present invention include, but are not limited to: MFold version 3.1 available from Genetics Corporation Group, Madison, Wis. (see Zucker et al., "Algorithms and Thermodynamics for RNA Secondary Structure Prediction: A Practical Guide," in *RNA Biochemistry and Biotechnology*, 11-43, J. Barciszewski & B. F. C. Clark, eds., NATO ASI Series, Kluwer Academic Publishers, Dordrecht, NL, (1999); Zucker et al., "Expanded Sequence Dependence of Thermodynamic Parameters Improves Prediction of RNA Secondary Structure," *J. Mol. Biol.* 288, 911-940 (1999); Zucker et al., "RNA Secondary Structure Prediction," in *Current Protocols in Nucleic Acid Chemistry*, S. Beaucage, D. E. Bergstrom, G. D. Glick, and R. A. Jones eds., John Wiley & Sons, New York, 11.2.1-11.2.10, (2000)), COVE (RNA structure analysis using covariance models (stochastic context free grammar methods)) v.2.4.2 (Eddy & Durbin, *Nucl. Acids Res.* 1994, 22:2079-2088) which is freely distributed as source code and which can be downloaded by accessing http:// www.genetics.wustl.edu/eddy/software/, and FOLDALIGN, also freely distributed and available for downloading at http:// www.bioinf.au.dk/FOLDALIGN/ (see Finding the most significant common sequence and structure motifs in a set of RNA sequences, J. Gorodkin, L. J. Heyer and G. D. Stormo, *Nucleic Acids Research*, Vol. 25, no. 18 pp 3724-3732, 1997; Finding Common Sequence and Structure Motifs in a set of RNA Sequences, J. Gorodkin, L. J. Heyer, and G. D. Stormo, *ISMB* 5:120-123, 1997).

The present invention is further described in the following examples, which are offered by way of illustration and are not intended to limit the invention in any manner.

EXAMPLES

Example 1

Plasmid Construction pPHAS-Fab1-HP: Hairpin RNAi was employed to decrease levels of KASII (also known as, and frequently referred to as, "Fab1" herein). The sense, antisense and intron fragments were assembled in the plasmid vector pGEM-T-Easy (Promega) before cloning into binary vector pDsRed-PHAS as PacI-XhoI fragment. A 178 by fragment from 5'UTR of exon 1 of At1g74960 (FAR1), which is not homologous to any other *Arabidopsis* sequences encoding KASI or KASIII enzymes, was amplified from *Arabidopsis* genomic DNA using oligonucleotides TTAATTAACGCATC-GAAGCTCTCTGCACGC (SEQ ID NO:1) and GCTAGCG-GCTTTGAGAAGAACCCAG (SEQ ID NO:2) and subsequently cloned into pGEM-T-Easy (Promega), such that the NheI site of the insert was adjacent to the PstI site of pGEM-T-Easy to create pGEM-T-Easy-HTM1.

Figure 2:
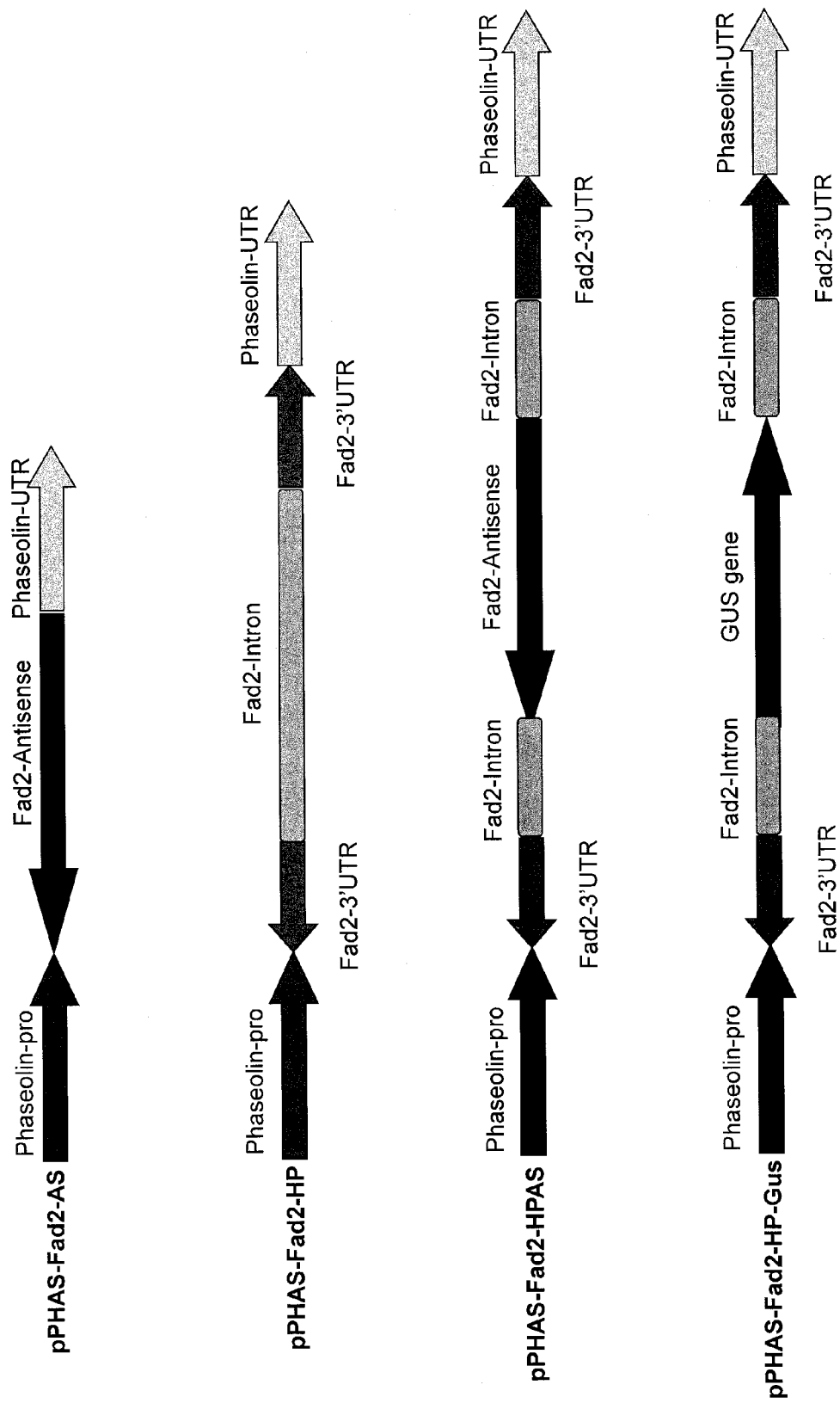
FIG. 2 is graphical representation of the constructs pPHAS-Fad2-AS, pPHAS-Fad2-HP, pPHAS-Fad2-HPAS, and pPHAS-Fad2-HP-GUS.
Figure 3:
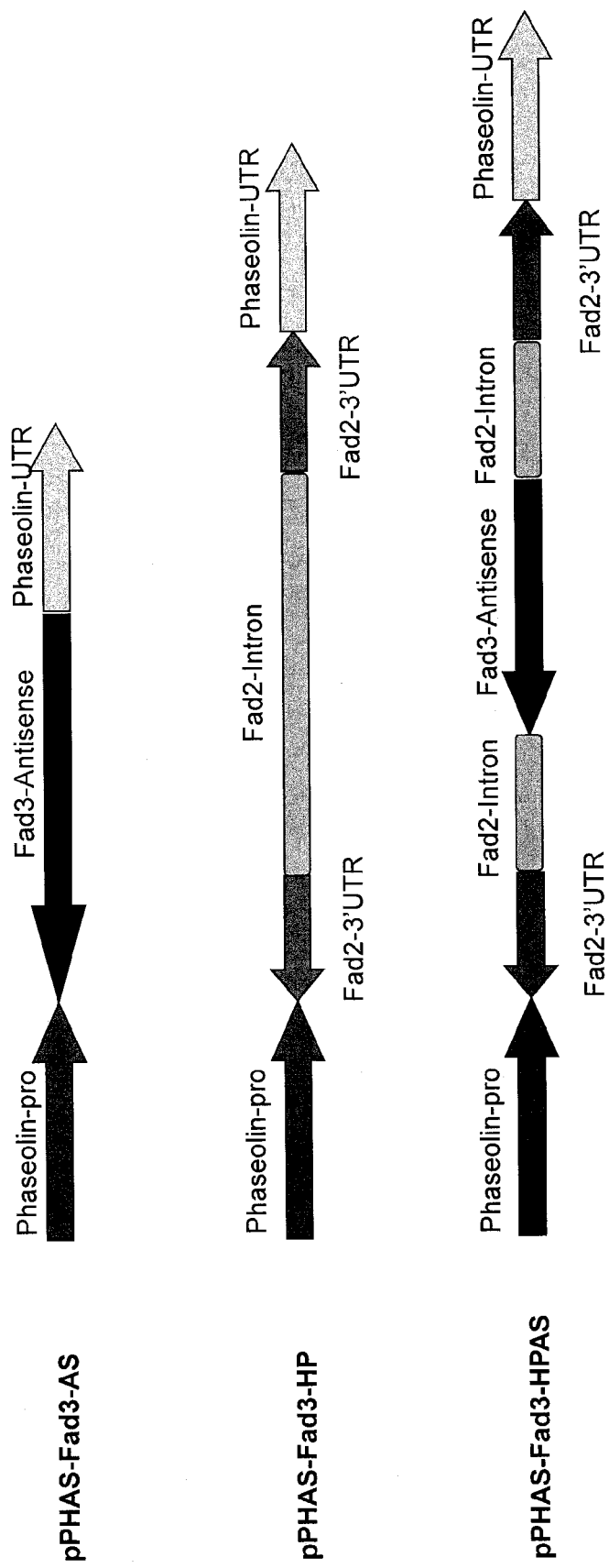
FIG. 3 is graphical representation of the constructs pPHAS-Fad3-AS, pPHAS-Fad3-HP, and pPHAS-Fad3-HPAS.

The first intron of FAD2 was then amplified using oligonucleotides GCTAGCGTCAGCTCCATCTCCAGGTCC (SEQ ID NO:3) and GCTAGCGTTTCTGCAGAAAAC-CAAAAGC (SEQ ID NO:4), such that this fragment contained 17 by of exon 1 and 4 by of exon 2 to ensure the inclusion of the 5' and 3' splice site. This fragment was then cloned into the PstI/NheI site of pGEM-T-Easy-HTM1 to create pGEM-T-Easy-HTM2. To complete the inverted repeat for Fab1 hairpin, the original 178 by 5'UTR fragment was amplified using primers CTGCAGAAAC-CCGGGCATCGAAGCTCTCTGCACGC (SEQ ID NO:5) and GAGCTCCTCGAGGGCTTTGAGAAGAACCCAG (SEQ ID NO:6), and cloned into the SacI/PstI site of pGEM-T-Easy-HTM2 to yield pGEM-T-Easy-HTM3. The resulting Fab1 hairpin sequence was excised from pGEM-T-Easy-HTM3 and inserted into pDs-red-PHAS as a PacTIXhoI fragment to produce pPHAS-FAB1-HP (FIG. 1).

pPHAS-Fab1-HPAS: 107 bp first exon of Fab1 gene was amplified from DNA genomic using primers KasII-5'exon-BglII (GGGAGATCTGGCGCGCCGGCTATCTC-CTCCACCGTGA (SEQ ID NO:7) and KasII-3'exon-SpeI (GGGACTAGTTCTTCCTTTTTATGCCATGG (SEQ ID NO:8)). The fragment was replaced with a part of Fad2-Intron at SpeI-BglII in pGEM-T-Easy-HTM3, then a cassette containing FAB1 hairpin, introns and Fab1 antisense was replaced with whole hairpin-intron of pPHAS-Fab1-HP, as represented in FIG. 1.

pPHAS-Fab1-AS: The 178 5'UTR of FAB1 gene above was amplified using primers KasII-5UTR-NheI/XhoI (GGCTCGAGCTAGCCGCATCGAAGCTCTCTGCACGC (SEQ ID NO:9)) and KasII-3UTR-PacI (GGTTAATTAAG-GCTTTGAGAAGAACCCAG (SEQ ID NO:10)). A fragment was replaced with whole Fab1 hairpin-intron in pPHAS-Fab 1-HP at PacI-XhoI, as represented in FIG. 1.

pPHAS-Fad2-HP: The 118 bp of 5'UTR sense and antisense of Fad2 uncoded sequences was amplified from genomic DNA and replaced with 5'UTR sense and antisense of KasII in pPHAS-Fab1-HP, as represented in FIG. 2.

pPHAS-Fad2-HPAS: 1152 by of Fad2 gene was amplified with primers FAD2-5'SphI (CGCATGCATGGGTGCAG-GTGGAAGAAT (SEQ ID NO:11)) and FAD2-3'SpeI (CCACTAGTTCATAACTTATTGTTGTACCA (SEQ ID NO:12)), the fragment was replaced with the part of Fad2 intron at SpeI-SphI in antisense direction, as represented in FIG. 2.

pPHAS-Fad2-AS: The Fad2 gene was amplified with primers FAD2-5'XhoI (CCCTCGAGATGGGTGCAGGTG-GAAGAAT (SEQ ID NO:13)) and FAD2-3'PacI (CCTTAAT-TAATCATAACTTATTGTTGTACCA (SEQ ID NO:14)), then replaced with Fad2-HP cassette in pPHAS -Fad2-HP at PacI-XhoI as antisense direction as represented in FIG. 3.

pPHAS-Fad3-HP: 138 bp of 3'UTR sense and antisense of Fad3 gene were amplified from genomic DNA. The fragments were replaced with 5'UTR sense and antisense of Fab1 in pPHAS-Fab1-HP, as represented in FIG. 3.

pPHAS-Fad3-HPAS: 301 bp first exon of Fad3 gene was amplified with primers Fad3-anti-5'BglII (GGAGATCTG-GCGCGCCCGTGGCCGAGAACAAAGATG (SEQ ID NO:15)) and Fad3-anti-3'SpeI (GGGACTAGTGTTGTTGC-TATGGACCAACGC (SEQ ID NO:16)), then replaced with a part of Fad2-intron at BglII-SpeI in antisense direction, as represented in FIG. 3.

pPHAS-Fad3-AS: The 301 bp first exon of Fad3 gene was amplified from DNA genomic using primers Fad3-anti-5'PacI (GGGTTAATTAACGTGGCCGAGAACAAAGATG (SEQ ID NO:17)) And Fad3-anti-3'XhoI (CCCTCGAGAGT-TGTTGCTATGGACCAACGC (SEQ ID NO:18)). The fragment was replaced with Fad3-HP cassette at PacI-XhoI, as represented in FIG. 3.

Example 2

*Arabidopsis* Cultivation and Transformation

*Arabidopsis* was cultivated under ~250uE of light with a photoperiod of 16/8 hours (light/dark) at 20° C. The vectors were introduced into *Agrobacterium tumefaciens* strain GV3101 pMP90 by electroporation and used to transform *Arabidopsis thaliana* plants by the floral dip method (N. Bechtold, J. Ellis, and G. Pelletier (1993), *C. R. Acad. Sci. Paris* 316, 1194-1198). Transformation was performed ~5 days after initial flowering.

Example 3

Determination of Fatty Acid Content in Seeds of *Arabidopsis*

Fatty Acid Analysis: Seeds were methylated (1 ml of 1 N HCl, methanol (Supelco), 80° C. for one hour), extracted with hexane and trimethylsilylated (100 µl of BSTFA-TMCS (bis (treimethylsilyl)trifluoroacetamidetrimethylsilane) (Supelco), 90° C. for 45 minutes). The BSTFA-TMCS was removed by evaporation and the sample was resuspended in hexane. Samples were analyzed on a Hewlett-Packard 6890 gas chromatograph equipped with a 5973 mass selective detector (GC/MS) and a SP-2340 cyano capillary column (Supelco) (60 m×250 µm×0.25 µm). The injector was held at 225° C., the oven temperature was varied (100-240° C. at 15° C./minute followed by 240° C. for five minutes), and the helium flow was 1.1 ml/minute. Assignment of peak identities was performed based on elution time versus authentic standards and validated based on their mass spectra. Quantitation was performed using Hewlett-Packard chemstation software.

Example 4

Modulation of Fatty Acid Synthesis in *Arabidopsis*

Figure 4:
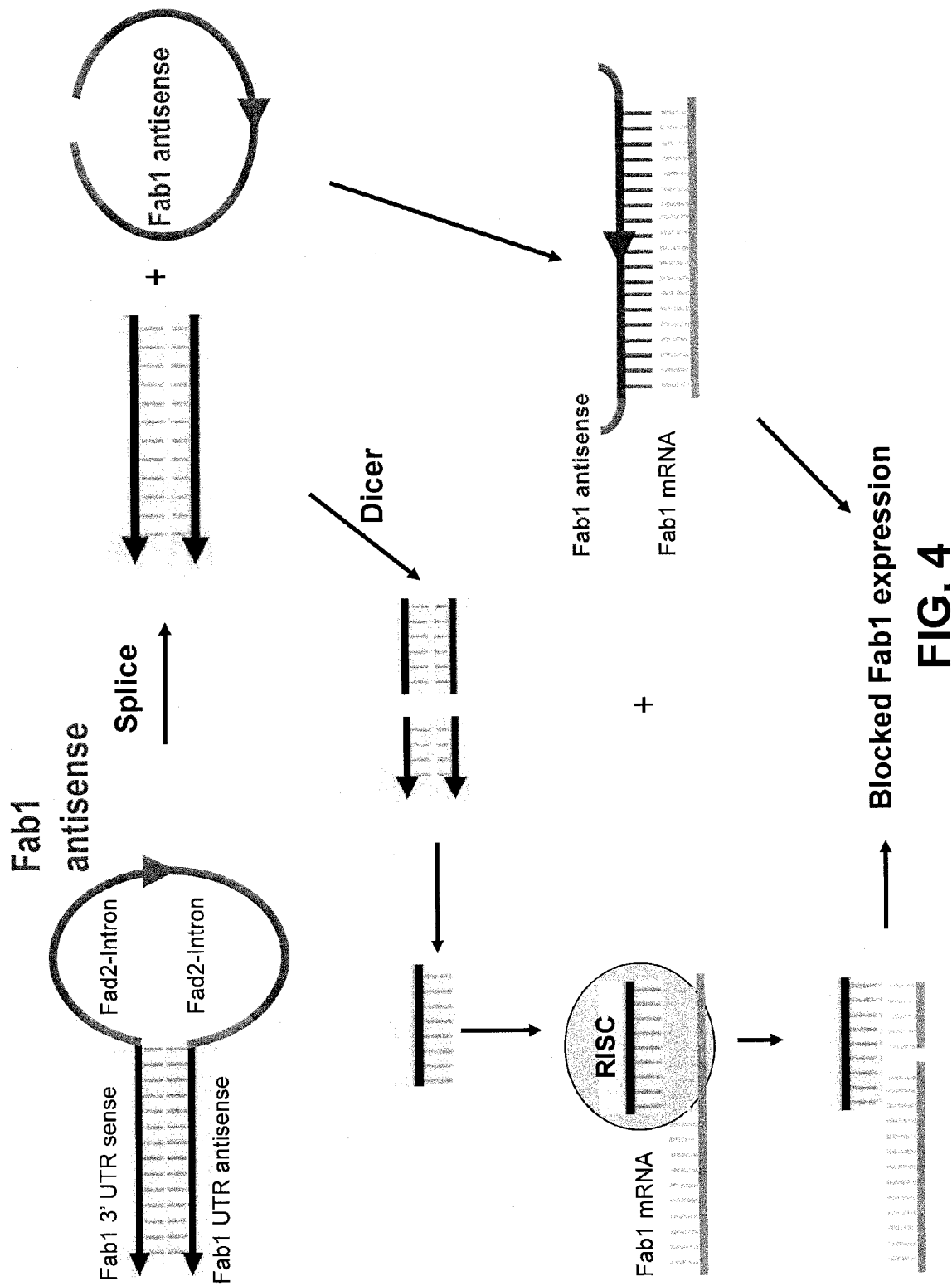
FIG. 4 is a diagram showing how the construct pPHAS-Fab1-HPAS may be processed in a cell to modulate expression of Fab1.

Three methods of gene suppression (antisense, hairpin RNAi, and hairpin RNAi with antisense) of the gene in the intron were compared. While not wishing to be bound by theory, mNAs containing hairpin RNAi and antisense sequences may be more potent in gene silencing through a model such as that depicted in FIG. 4. In the model of FIG. 4, upon splicing of the intron to create the siRNA, a DNA fragment containing an antisense portion of the gene would be created, thus providing an additional potential method of reduction of gene expression in addition to the RNAi, dicer substrate that is generated.

Figure 5:
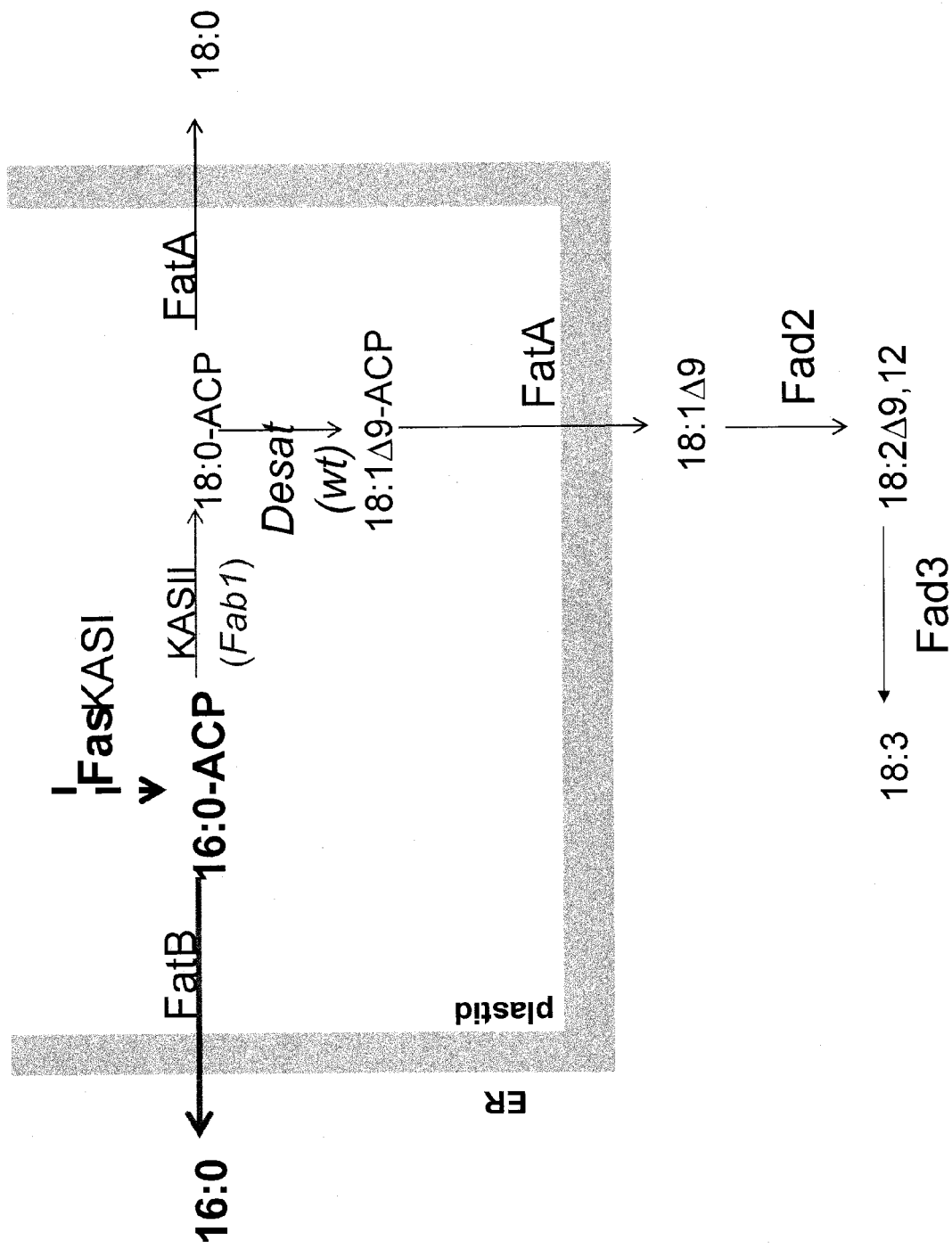
FIG. 5 is a schematic diagram of fatty acid production in *Arabidopsis*.

Three genes were chosen for the comparison of the three methods of gene suppression (the 12-desaturase FAB2 and the 15-desaturase FAD3 because they are easily scored; and the FAD2 because it had been used before for evaluation of reduction in gene expression), as well as β-ketoacyl-ACP synthase (KAS) II. The relationship between these enzymes and fatty acid synthesis in *Arabidopsis* is depicted in FIG. 5.

In addition to being the target tissue for modification of fatty acid content of oil seed crops, seeds provide a reliable source of material for reproducibly analyzing the results of transformations carried out using the constructs created in Example 1. Thus, the fatty acid content of seeds from the transformed plants was analyzed by gas chromatography and mass spectrometric analysis to qualitatively confine the assignments of peaks as specific fatty acids. Student T-test was used to assign significance to differences between means (based on ten or more samples per mean). The results for the constructs created in Example 1 are represented in Examples 5-8 below.

Example 5

Modulation of FAB1 Expression

Figure 6:
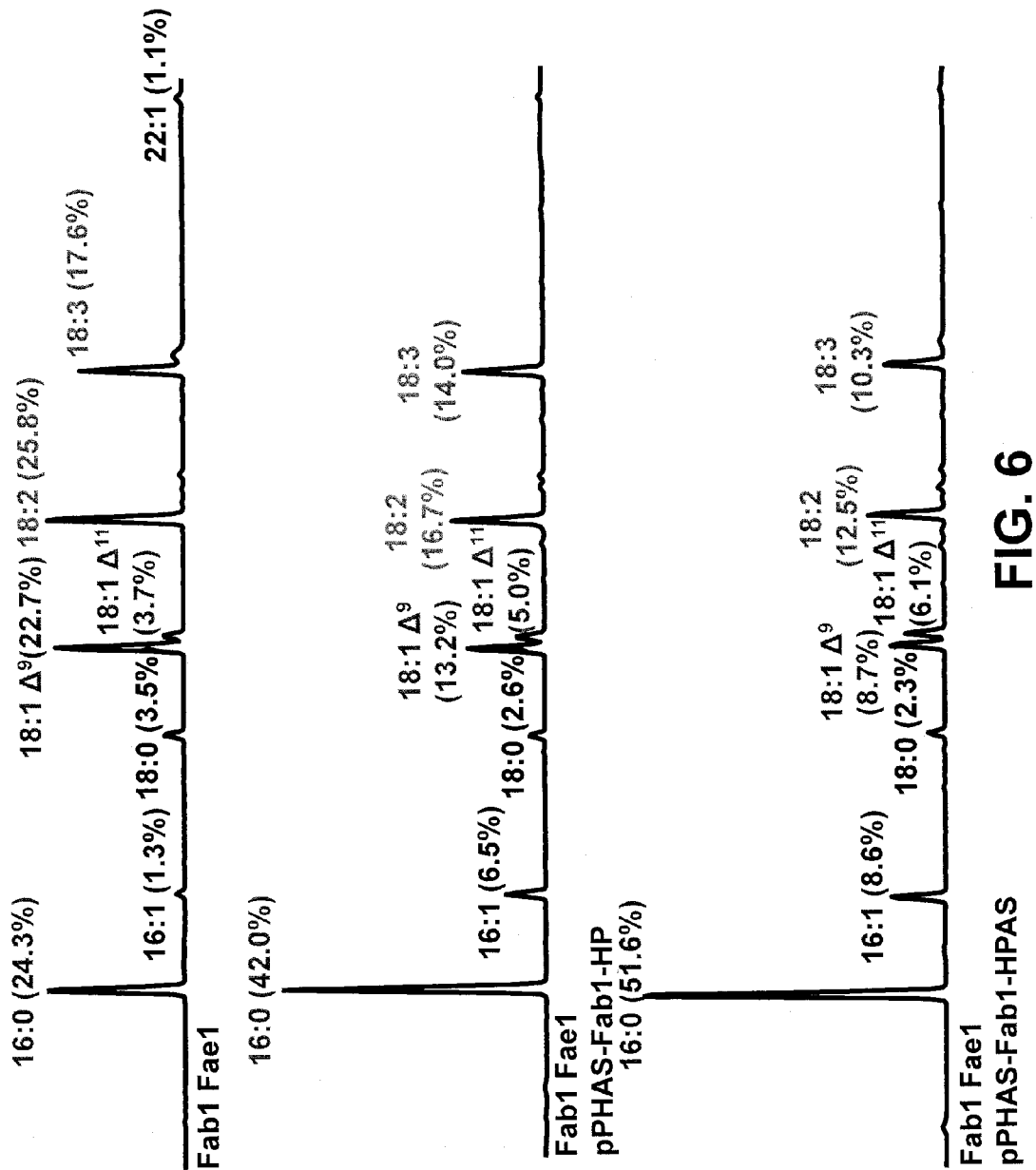
FIG. 6 shows gas chromatograph traces indicating the levels of various fatty acids in seeds containing pPHAS-Fab1-HP and pPHAS-Fab1-HPAS as compared to the background strain.
Figure 7:
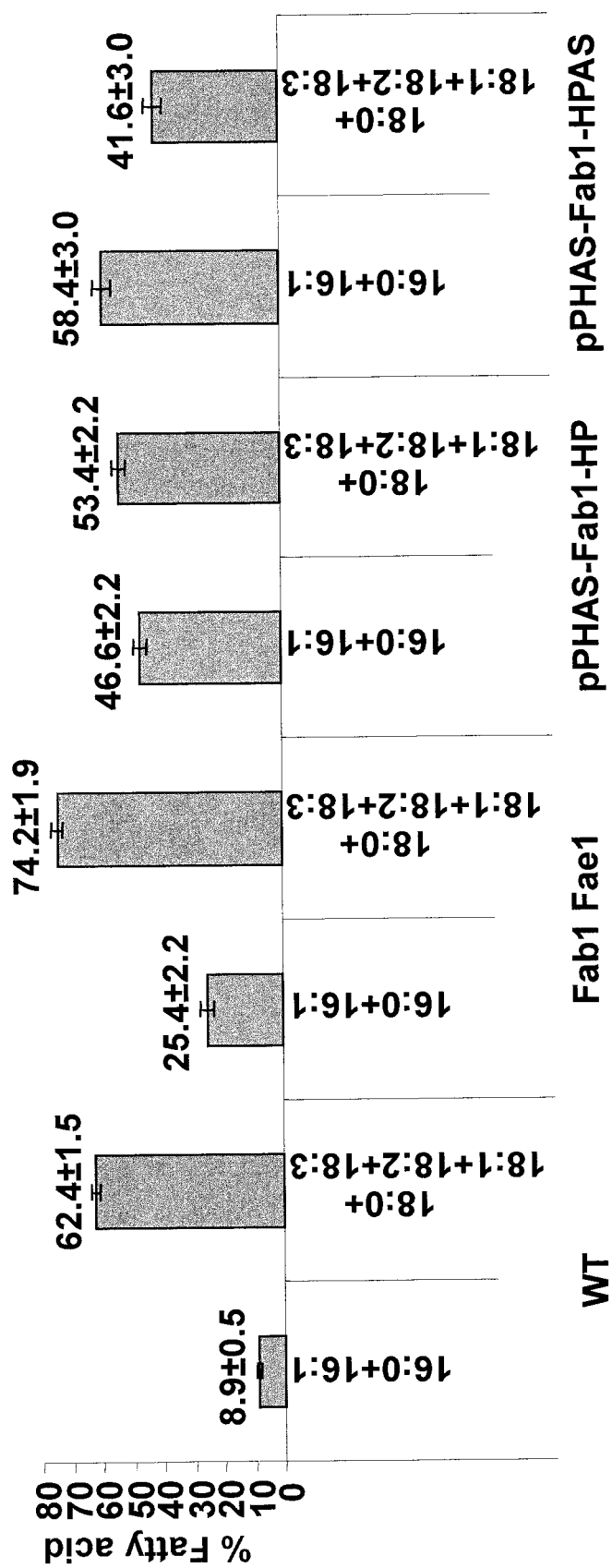
FIG. 7 is a graphical summary indicating the levels of various fatty acids in seeds containing pPHAS-Fab1-HP and pPHAS-Fab1-HPAS as compared to the background strain.

FAB1 elongates 16 C atom (C16) to 18 C atom (C18) fatty acids in the plastid. For FAB1, levels of 16:0 plus 16:1 fatty acids (the substrates for FAB1) were compared with the levels of its product 18:0 and 18:1 plus metabolites 18:2 and 18:3. Wild-type *Arabidopsis* was compared to the fab1 fae1 mutant line and with the fab1 fae1 mutant line transformed with either the FAB1 hairpin (Fab1-HP) or with the FAB1 including the combined hairpin and antisense (fab1-HPAS). The results are presented in FIG. 6 and graphically summarized in FIG. 7. The fab1 fae1 line showed a significant increase in C18 fatty acids due to the fae1 mutation which blocks further elongation to the 20C level. Introduction of the fab1-HP into the fab1 fae1 mutant background decreased the C18 fatty acids from 74.2% to 53.4%, whereas introduction of the fab1-HPAS construct resulted in a decrease to 41.6% 18C fatty acids.

Example 6

Modulation of FAD2 Expression

Figure 8:
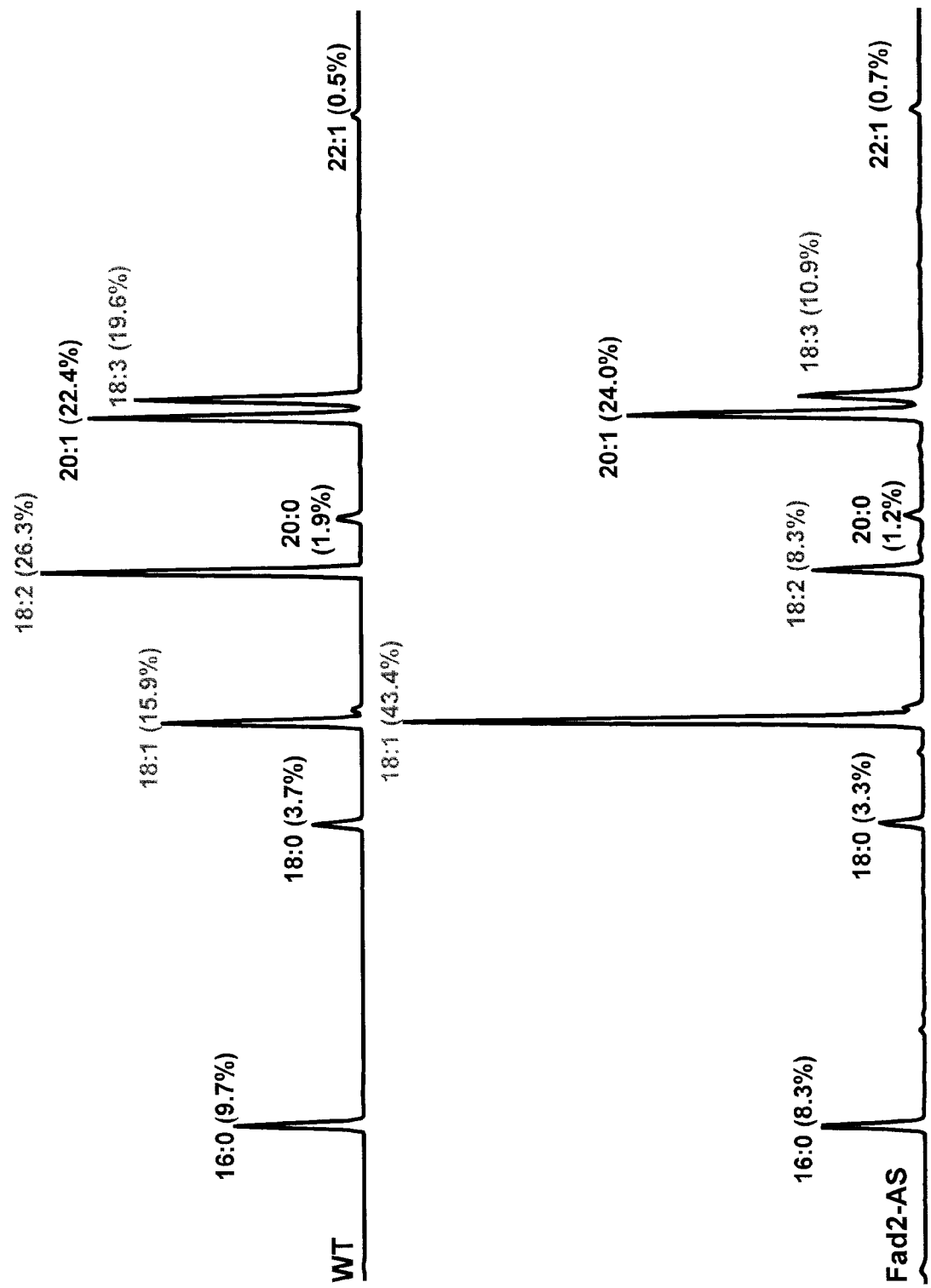
FIG. 8 shows gas chromatograph traces indicating the levels of various fatty acids in seeds containing pPHAS-Fad2-AS as compared to wild-type.
Figure 9:
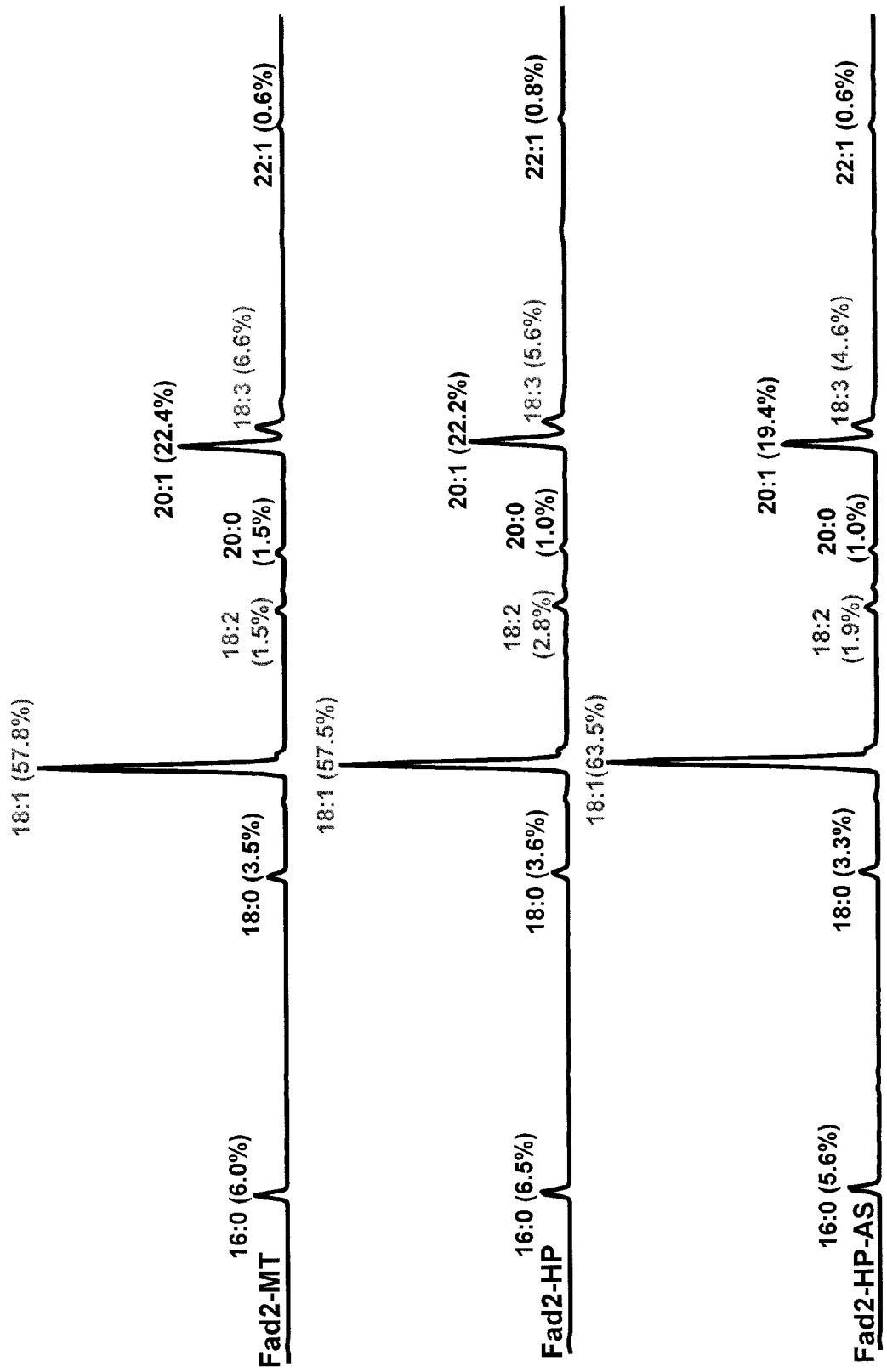
FIG. 9 shows gas chromatograph traces indicating the levels of various fatty acids in seeds containing pPHAS-Fad2-HP and pPHAS-Fad2-HPAS as compared to the Fad2-MT mutant.
Figure 10:
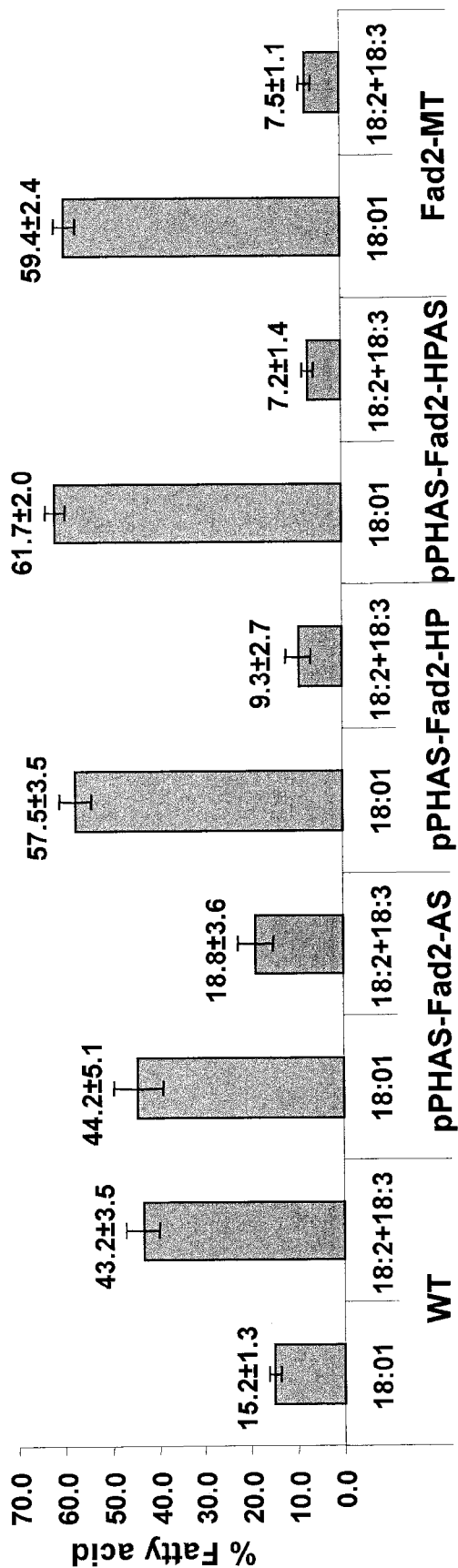
FIG. 10 is a graphical summary indicating the levels of various fatty acids in seeds containing pPHAS-Fad2-AS, pPHAS-Fad2-HP, and pPHAS-Fad2-HPAS as compared to the Fad2-MT mutant and the background strain.

For FAD2, levels of 18:1 fatty acids (the substrate for FAD2) were compared with the levels of its product 18:2 and the metabolite 18:3. For analysis, 18:2 was summed with 18:3 to estimate the total fatty acid proportion that had been desaturated by FAD2. Wild-type *Arabidopsis* was compared to FAD2-antisense (Fad2-AS), FAD2 hairpin RNAi (Fad2-HP), and FAD2 was compared with the combined hairpin and antisense (Fad2-HPAS). Each of these was compared to the most severe FAD2 mutant, FAD2-2 (Fad2-MT). The results are presented in FIGS. 8 and 9 and graphically summarized in FIG. 10.

WT levels of 18:2+18:3 were 43%, which declined to 18.9% in the Fad2-AS, and to 9.4% in the Fad2-HP line. Both changes were significant at the P<0.01 level. The decline from 9.4% in the Fad2-HP line to 7.2% in the Fad2-HPAS line was significant at the P<0.05 level. The 7.2% in the Fad2-HPAS line was not significantly different from that of the fad2-MT at 7.5%.

Example 7

Modulation of FAD2 Expression with Introduction of GUS Expression

Figure 11:
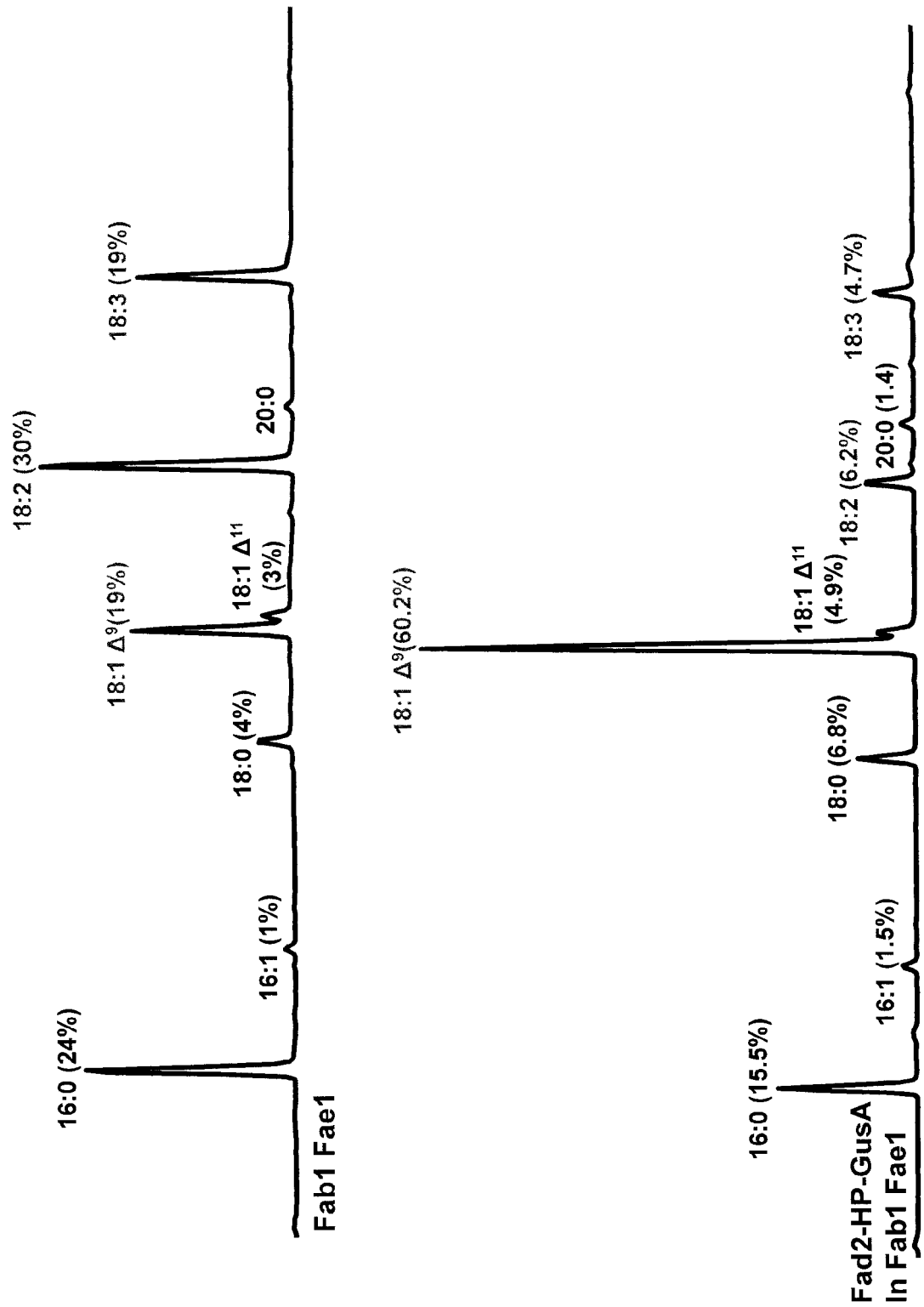
FIG. 11 shows gas chromatograph traces indicating the levels of various fatty acids in seeds containing pPHAS-Fad2-HP-GUS as compared to the background strain.
Figure 12:
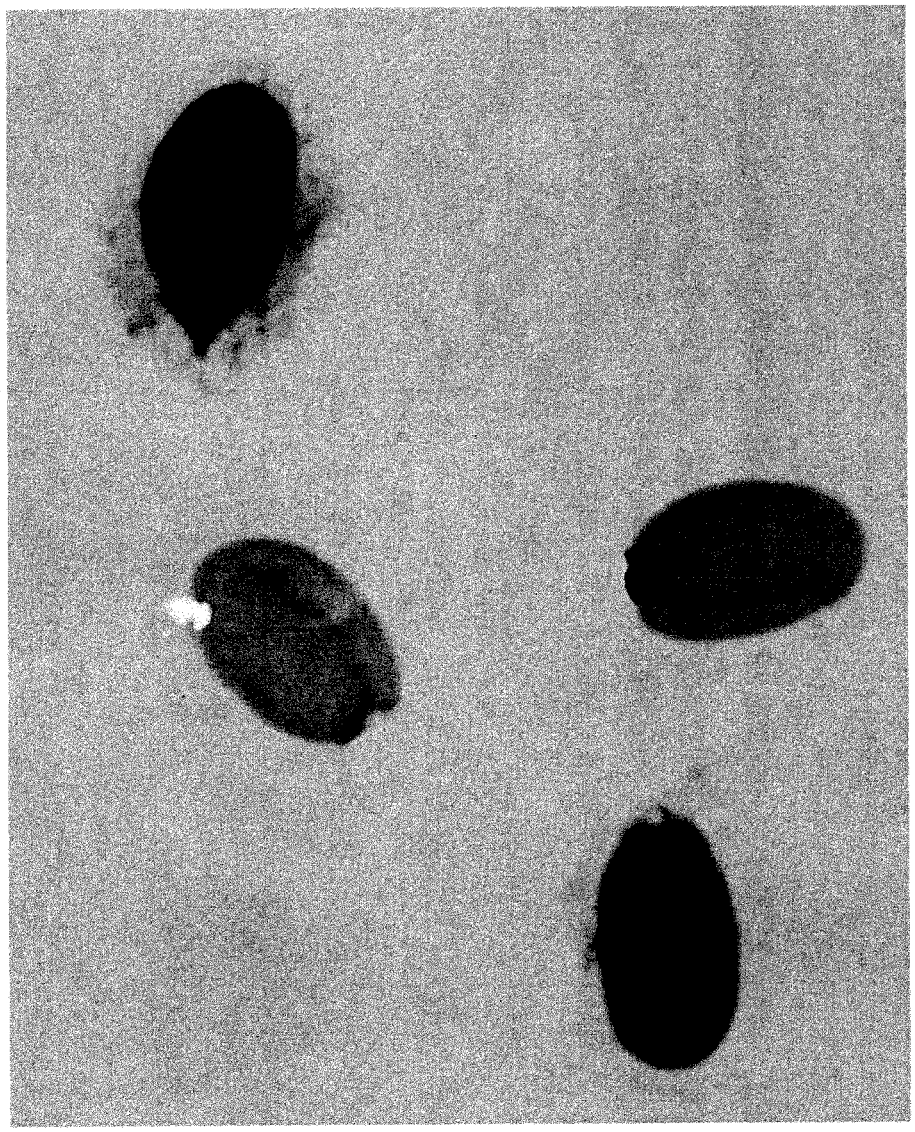
FIG. 12 shows a photograph containing wild-type seeds (lighter seeds) and seeds expressing GUS from pPHAS-Fad2-HP-GUS (darker seeds).

For FAD2, levels of 18:1 fatty acids (the substrate for FAD2) were compared with the levels of its product 18:2 and the metabolite 18:3. For analysis, 18:2 was summed with 18:3 to get the total fatty acid proportion that had been desaturated by FAD2. Wild-type *Arabidopsis* was compared to FAD2 hairpin RNAi containing the GUS gene in the intron (Fad2-HP-GUS). The results are presented in FIGS. 11 and 12.

WT levels of 18:2+18:3 were 49%, which declined to 12.3% in the Fad2-HP-GUS. The change was significant at the P<0.01 level. In addition, blue staining for GUS was apparent in transformed seeds, indicating expression of GUS in those seeds.

Example 8

Modulation of FAD3 Expression

Figure 13:
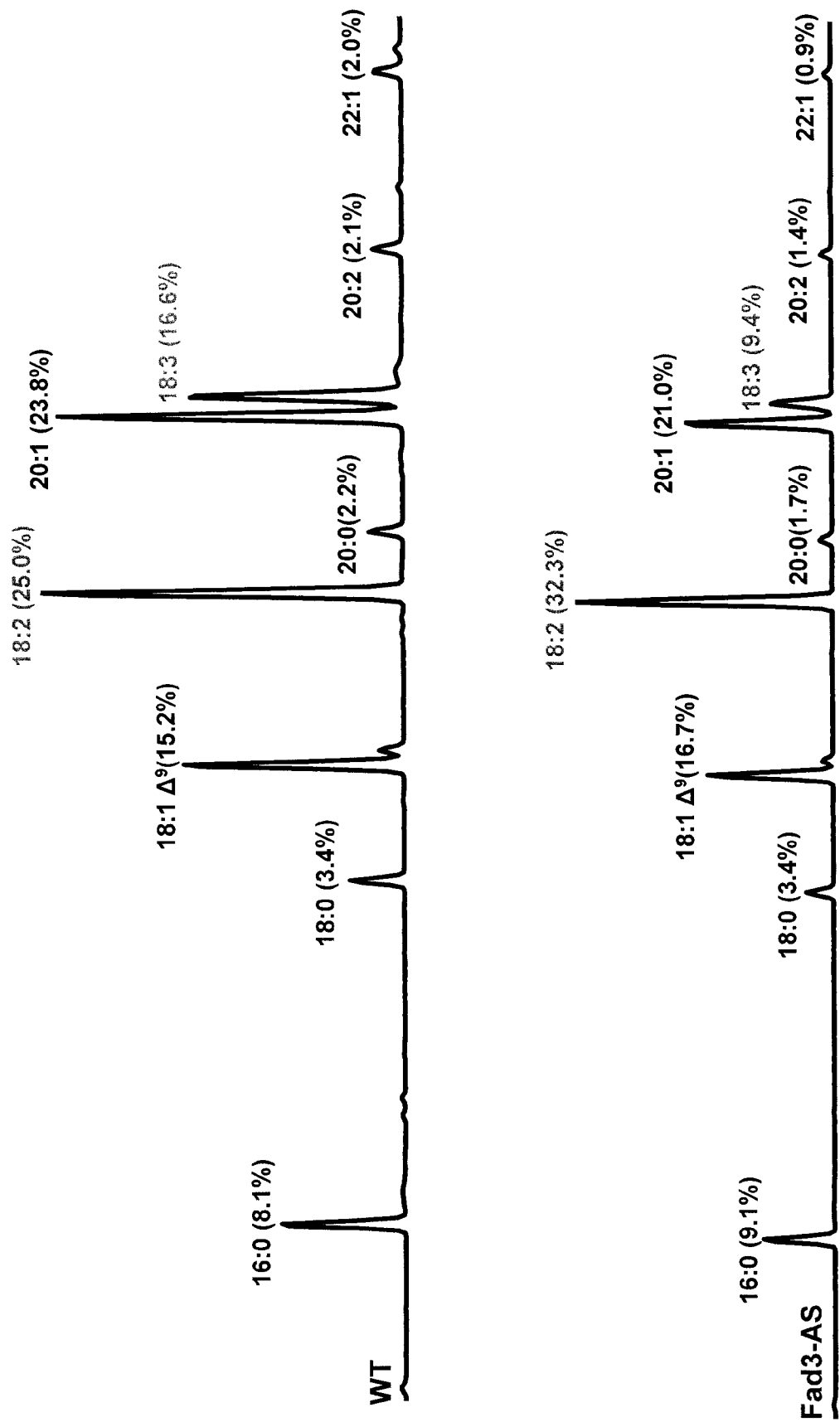
FIG. 13 shows gas chromatograph traces indicating the levels of various fatty acids in seeds containing pPHAS-Fad3-AS as compared to wild-type.
Figure 14:
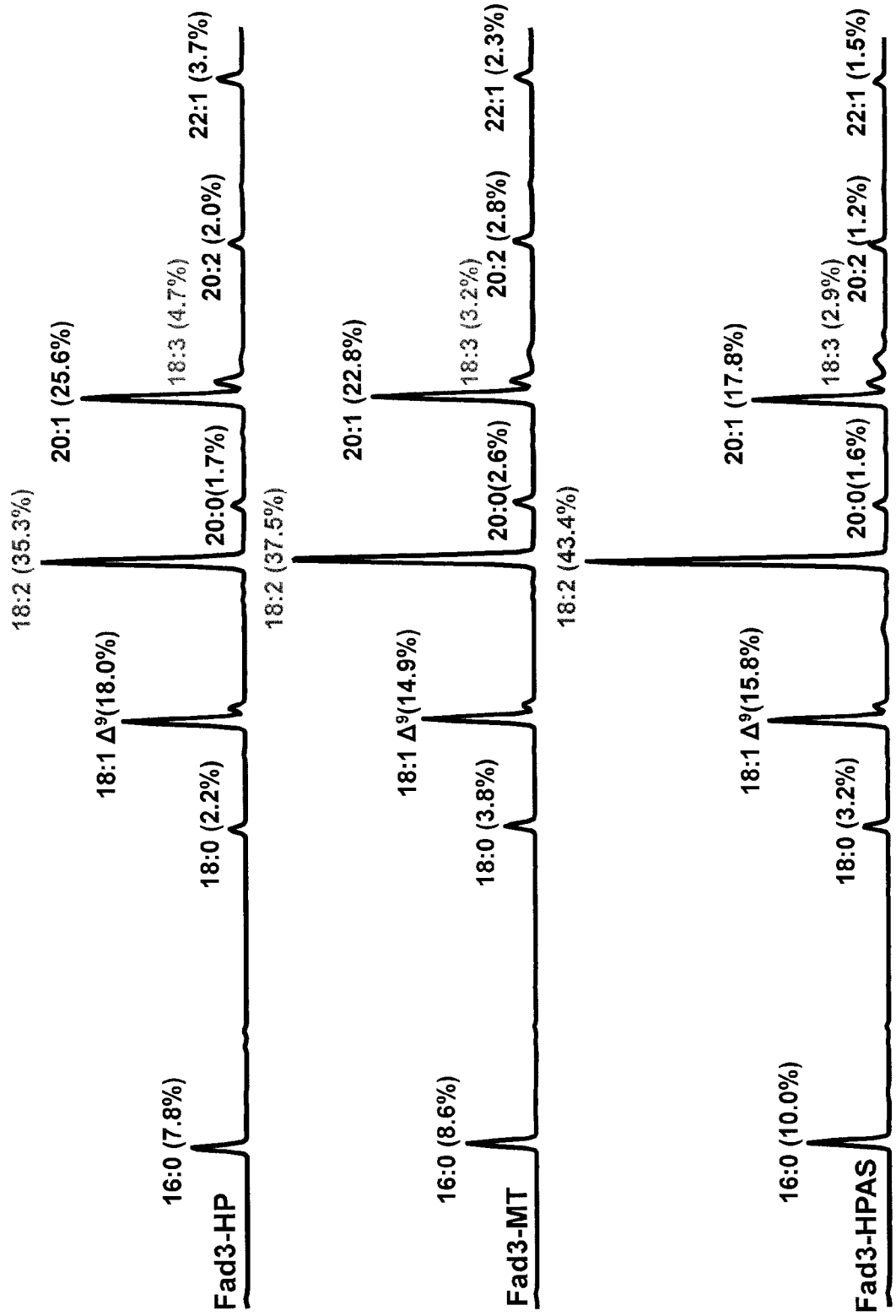
FIG. 14 shows gas chromatograph traces indicating the levels of various fatty acids in seeds containing pPHAS-Fad3-HP and pPHAS-Fad3-HPAS as compared to the Fad3-MT mutant.
Figure 15:
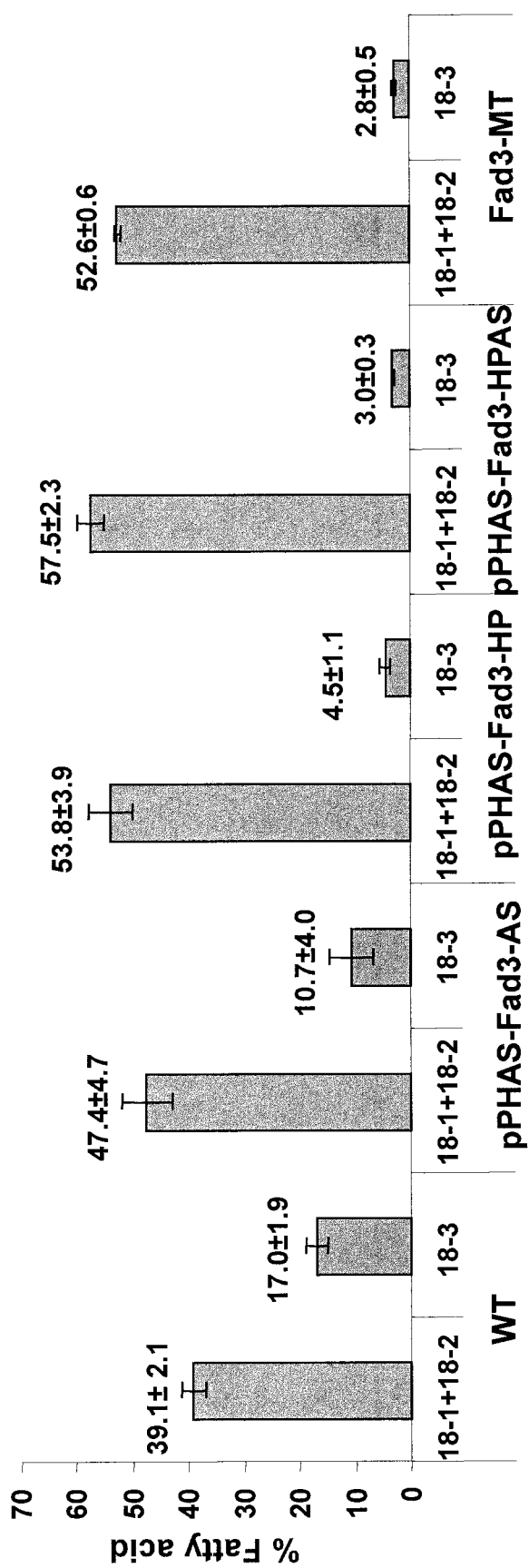
FIG. 15 is a graphical summary indicating the levels of various fatty acids in seeds containing pPHAS-Fad3-AS, pPHAS-Fad3-HP, and pPHAS-Fad3-HPAS as compared to the Fad3-MT mutant and the background strain.

For FAD3, levels of 18:1 plus 18:2 fatty acids (18:2 being the substrate for FAD3) were compared with the levels of its product 18:3. Wild-type *Arabidopsis* was compared to FAD3-antisense (Fad3-AS), to FAD3 hairpin (RNAi Fad3-HP), and to FAD3 with the combined hairpin and antisense (Fad3-HPAS). The results are presented in FIGS. 13 and 14 and graphically summarized in FIG. 15.

WT levels of 18:3 were 17.0%, declined to 10.7% in the Fad3-AS, 4.5% in the Fad3-HP line and 3.0% in the Fad3-HPAS line. All of the treatments were significantly different from all other treatments at the P<0.01 level. The Fad3-HPAS line at 3.0% was not significantly different from the strongest mutant Fad3 allele, Fad3-3, at 2.8%.

While this invention has been described in certain example embodiments, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

All references, including publications, patents, and patent applications, cited herein are hereby incorporated by reference to the same extent as if each reference were individually and specifically indicated to be incorporated by reference and were set forth in its entirety herein. The references discussed herein are provided solely for their disclosure prior to the filing date of the present application. Nothing herein is to be construed as an admission that the inventors are not entitled to antedate such disclosure by virtue of prior invention.

What is claimed is:

1. A nucleotide construct comprising:
   a nucleotide sequence that forms a stem and at least two loops;
   wherein at least one of the least two loops comprises a first nucleotide sequence that modulates expression of a target;
   wherein the stem comprises a second nucleotide sequence that modulates expression of a target;
   wherein both the first and second nucleotide sequence modulate the expression of a target via binding to a target;
   wherein the first nucleotide sequence and the second nucleotide sequence are not contiguous;
   wherein the first nucleotide sequence is located entirely within at least one of the least two loops; and
   wherein the target modulated by the first nucleotide sequence and the target modulated by the second nucleotide sequence may be the same or different.

2. The nucleotide construct of claim 1, wherein the second nucleotide sequence that modulates expression of a target modulates the expression of the target through an RNAi pathway.

3. The nucleotide construct of claim 1, wherein the first nucleotide sequence that modulates expression of a target modulates the expression of the target via antisense modulation of expression.

4. The nucleotide construct of claim 1, further comprising a gene of interest operably linked to a promoter, and wherein the loop comprising the first nucleotide sequence may or may not comprise a nucleotide sequence that modulates expression of a target.

5. The nucleotide construct of claim 4, wherein the gene of interest operably linked to a promoter is located in the loop comprising the first nucleotide sequence.

6. The nucleotide construct of claim 1, further comprising one or more splice sites in the loop comprising the first nucleotide sequence.

7. The nucleotide construct of claim 1, wherein the loop comprising the first nucleotide sequence contains more than one nucleotide sequence that modulates expression of a target.

8. The nucleotide construct of claim 1, wherein the stem contains more than one nucleotide sequence that modulates expression of a target.

9. The nucleotide construct of claim 1, wherein the stem contains one or more nucleotide sequences that regulate expression of one or more targets and wherein the loop comprising the first nucleotide sequence contains one or more nucleotide sequences that regulate expression of one or more targets.

10. The nucleotide construct of claim 1, wherein the nucleotide construct comprises a PNA.

11. The nucleotide construct of claim 1, wherein the nucleotide construct comprises a synthetic base.

12. The nucleotide construct of claim 1, wherein the nucleotide construct comprises a modified sugar.

13. The nucleotides construction of claim 1, wherein the stem comprises a miRNA.

14. The nucleotides construction of claim 1, wherein at least one loop comprises a miRNA.

15. A vector comprising the nucleotide construct of claim 1 operably linked to a promoter.

16. The vector of claim 15, wherein the promoter is selected from the group consisting of viral, retroviral, mammalian, plant, bacterial, constitutive, regulatable, fungal, yeast, and insect promoters.

17. The vector of claim 16, wherein the plant promoter is selected from the group consisting of promoters identified in Arabidopsis, sunflower, cotton, rapeseed, maize, wheat, castor, palm, tobacco, peanut, sorghum, sugarcane, and soybean.

18. The vector of claim 15, wherein the vector is selected from the group consisting of plasmids, cosmids, retroviral vectors, agrobacterium, viral vectors, bacterial vectors, yeast vectors, eukaryotic vectors, plant vectors, and mammalian vectors.

19. The vector of claim 15, further comprising sequences that promote the integration into a genome of the nucleotide construct of claim 1 operably linked to a promoter.

20. A method of regulating the expression of a target, the method comprising:
providing to a cell the nucleotide construct of claim 1; and
culturing said cell.

21. The method according to claim 20, wherein the cell is selected from the group consisting of prokaryotic, eukaryotic, bacterial, agrobacterium, yeast, plant, mammalian, and human cells.

22. The method according to claim 21, herein the plant cell is selected from the group consisting of promoters identified in Arabidopsis, sunflower, cotton, rapeseed, maize, wheat, castor, palm, tobacco, peanut, sorghum, sugarcane, and soybean cells.

23. The method according to claim 20, wherein the target is a gene, oligonucleotide sequence, and/or a protein.

24. A method of regulating the expression of a target, the method comprising:
providing to a cell a vector comprising the vector of claim 15; and
expressing the nucleotide construct of claim 1 from said vector in said cell.

25. The method according to claim 24, wherein the target is a gene, oligonucleotide sequence, and/or a protein.

26. The method according to claim 24, wherein the cell is selected from the group consisting of prokaryotic, eukaryotic, bacterial, agrobacterium, yeast, plant, mammalian, and human cells.

27. The method according to claim 26, wherein the plant cell is selected from the group consisting of Arabidopsis, sunflower, cotton, rapeseed, maize, wheat, castor, palm, tobacco, peanut, sorghum, sugarcane, and soybean cells.

28. A cell comprising the nucleotide construct of claim 1.

29. The cell according to claim 28, wherein the cell is selected from the group consisting of prokaryotic, eukaryotic, bacterial, agrobacterium, yeast, plant, mammalian, and human cells.

30. The cell according to claim 29 wherein the plant is selected from the group consisting of Arabidopsis, sunflower, cotton, rapeseed, maize, wheat, castor, palm, tobacco, peanut, sorghum, sugarcane, and soybean.

31. The nucleotide construct according to claim 1, wherein the target modulated by the first nucleotide sequence, the target modulated by the second nucleotide sequence, or both are a nucleic acids involved in fatty acid synthesis.

32. The nucleotide construct according to claim 1, wherein the construct is present in a cell comprising the target modulated by the first nucleotide sequence and the target modulated by the second nucleotide sequence.

33. A nucleotide construct comprising:
a nucleotide sequence that forms a stem and at least two loops;
wherein at least one of the at least two loops comprises a first nucleotide sequence that modulates expression of a target;
wherein the stem comprises a second nucleotide sequence that modulates expression of a target;
wherein both the first and second nucleotide sequence modulate the expression of a target via binding to a target;
wherein the target modulated by the first nucleotide sequence and the target modulated by the second nucleotide sequence may be the same or different;
wherein the first nucleotide sequence is located entirely within the loop comprising the first nucleotide sequence; and
wherein the first nucleotide sequence and the second nucleotide sequence each comprise an antisense sequences capable of modulating the expression of a gene selected from the group consisting of FAB1, FAD2, and FAD3.

34. The nucleotides construction of claim 33, wherein the stem comprises a miRNA.

35. The nucleotides construction of claim 33, wherein at least one loop comprises a miRNA.

36. A nucleotide construct comprising:
a nucleotide sequence that forms a stem and at least two loops;
wherein at least one of the at least two loops comprises a first nucleotide sequence of at least ten contiguous bases that are complementary to a target;
wherein the stem comprises a second nucleotide sequence of at least ten contiguous bases that are complementary to a target;
wherein both the first and second nucleotide sequence are able to hybridize with a target;
wherein the first nucleotide sequence and the second nucleotide sequence are not contiguous;
wherein the first nucleotide sequence is located entirely within the loop comprising the first nucleotide sequence; and wherein the target of the first nucleotide sequence and the target of the second nucleotide sequence may be the same or different.

37. The nucleotides construction of claim 36, wherein the stem comprises a miRNA.

38. The nucleotides construction of claim 36, wherein at least one loop comprises a miRNA.

39. A nucleotide construct comprising:
a nucleotide sequence that forms a stem and at least two loops;
wherein at least one of the at least two loops comprises a first nucleotide sequence that modulates expression of a target;
wherein the stem comprises a second nucleotide sequence that modulates expression of a target;
wherein both the first and second nucleotide sequence modulate the expression of a target via binding to a target;
wherein the first nucleotide sequence and the second nucleotide sequence are not contiguous;
wherein the first nucleotide sequence is located entirely within the loop comprising the first nucleotide sequence;
wherein the nucleotide construct comprises splice sites configured so as to allow at least a portion of the loop comprising the first nucleotide sequence to be spliced away from the stem; and
wherein the target modulated by the first nucleotide sequence and the target modulated by the second nucleotide sequence may be the same or different.

40. The nucleotides construction of claim 39, wherein the stem comprises a miRNA.

41. The nucleotides construction of claim 40, wherein at least one loop comprises a miRNA.

* * * * *

SEQUENCE LISTING

<160> NUMBER OF SEQ ID NOS: 18

<210> SEQ ID NO 1
<211> LENGTH: 30
<212> TYPE: DNA
<213> ORGANISM: Artificial
<220> FEATURE:

<223> OTHER INFORMATION: Primer

<400> SEQUENCE: 1
ttaattaacg catcgaagct ctctgcacgc                              30

<210> SEQ ID NO 2
<211> LENGTH: 25
<212> TYPE: DNA
<213> ORGANISM: Artificial
<220> FEATURE:
<223> OTHER INFORMATION: Primer

<400> SEQUENCE: 2
gctagcggct ttgagaagaa cccag                                   25

<210> SEQ ID NO 3
<211> LENGTH: 27
<212> TYPE: DNA
<213> ORGANISM: Artificial
<220> FEATURE:
<223> OTHER INFORMATION: Primer

<400> SEQUENCE: 3
gctagcgtca gctccatctc caggtcc                                 27

<210> SEQ ID NO 4
<211> LENGTH: 28
<212> TYPE: DNA
<213> ORGANISM: Artificial
<220> FEATURE:
<223> OTHER INFORMATION: Primer

<400> SEQUENCE: 4
gctagcgttt ctgcagaaaa ccaaaagc                                28

<210> SEQ ID NO 5
<211> LENGTH: 35
<212> TYPE: DNA
<213> ORGANISM: Artificial
<220> FEATURE:
<223> OTHER INFORMATION: Primer

<400> SEQUENCE: 5
ctgcagaaac ccgggcatcg aagctctctg cacgc                        35

<210> SEQ ID NO 6
<211> LENGTH: 31
<212> TYPE: DNA
<213> ORGANISM: Artificial
<220> FEATURE:
<223> OTHER INFORMATION: Primer

<400> SEQUENCE: 6
gagctcctcg agggctttga gaagaaccca g                            31

<210> SEQ ID NO 7
<211> LENGTH: 37
<212> TYPE: DNA
<213> ORGANISM: Artificial
<220> FEATURE:
<223> OTHER INFORMATION: Primer

<400> SEQUENCE: 7
gggagatctg gcgcgccggc tatctcctcc accgtga                      37

```
<210> SEQ ID NO 8
<211> LENGTH: 29
<212> TYPE: DNA
<213> ORGANISM: Artificial
<220> FEATURE:
<223> OTHER INFORMATION: Primer

<400> SEQUENCE: 8
gggactagtt cttccttttt atgccatgg                                       29

<210> SEQ ID NO 9
<211> LENGTH: 35
<212> TYPE: DNA
<213> ORGANISM: Artificial
<220> FEATURE:
<223> OTHER INFORMATION: Primer

<400> SEQUENCE: 9
ggctcgagct agccgcatcg aagctctctg cacgc                                35

<210> SEQ ID NO 10
<211> LENGTH: 29
<212> TYPE: DNA
<213> ORGANISM: Artificial
<220> FEATURE:
<223> OTHER INFORMATION: Primer

<400> SEQUENCE: 10
ggttaattaa ggctttgaga agaacccag                                       29

<210> SEQ ID NO 11
<211> LENGTH: 27
<212> TYPE: DNA
<213> ORGANISM: Artificial
<220> FEATURE:
<223> OTHER INFORMATION: Primer

<400> SEQUENCE: 11
cgcatgcatg ggtgcaggtg gaagaat                                         27

<210> SEQ ID NO 12
<211> LENGTH: 29
<212> TYPE: DNA
<213> ORGANISM: Artificial
<220> FEATURE:
<223> OTHER INFORMATION: Primer

<400> SEQUENCE: 12
ccactagttc ataacttatt gttgtacca                                       29

<210> SEQ ID NO 13
<211> LENGTH: 28
<212> TYPE: DNA
<213> ORGANISM: Artificial
<220> FEATURE:
<223> OTHER INFORMATION: Primer

<400> SEQUENCE: 13
ccctcgagat gggtgcaggt ggaagaat                                        28

<210> SEQ ID NO 14
<211> LENGTH: 31
<212> TYPE: DNA
<213> ORGANISM: Artificial
```

```
<220> FEATURE:
<223> OTHER INFORMATION: Primer

<400> SEQUENCE: 14
ccttaattaa tcataactta ttgttgtacc a                                              31

<210> SEQ ID NO 15
<211> LENGTH: 36
<212> TYPE: DNA
<213> ORGANISM: Artificial
<220> FEATURE:
<223> OTHER INFORMATION: Primer

<400> SEQUENCE: 15
ggagatctgg cgcgcccgtg gccgagaaca aagatg                                         36

<210> SEQ ID NO 16
<211> LENGTH: 30
<212> TYPE: DNA
<213> ORGANISM: Artificial
<220> FEATURE:
<223> OTHER INFORMATION: Primer

<400> SEQUENCE: 16
gggactagtg ttgttgctat ggaccaacgc                                                30

<210> SEQ ID NO 17
<211> LENGTH: 31
<212> TYPE: DNA
<213> ORGANISM: Artificial
<220> FEATURE:
<223> OTHER INFORMATION: Primer

<400> SEQUENCE: 17
gggttaatta acgtggccga gaacaaagat g                                              31

<210> SEQ ID NO 18
<211> LENGTH: 30
<212> TYPE: DNA
<213> ORGANISM: Artificial
<220> FEATURE:
<223> OTHER INFORMATION: Primer

<400> SEQUENCE: 18
ccctcgagag ttgttgctat ggaccaacgc                                                30
```